United States Patent [19]

Oguni et al.

[11] Patent Number: 5,457,225
[45] Date of Patent: Oct. 10, 1995

[54] PROCESS FOR PREPARATION OF 5-HYDROXY-3-KETOESTER DERIVATIVE AND OPTICALLY ACTIVE SUBSTANCE THEREOF

[75] Inventors: Nobuki Oguni; Masahiko Hayashi; Katsumasa Harada, all of Yamaguchi; Akio Matsushita, Yamagushi, all of Japan

[73] Assignee: Ube Industries Ltd., Yamaguchi, Japan

[21] Appl. No.: 302,342

[22] Filed: Sep. 7, 1994

[30] Foreign Application Priority Data

Sep. 7, 1993 [JP] Japan .................................. 5-222583
Sep. 7, 1993 [JP] Japan .................................. 5-222584

[51] Int. Cl.$^6$ .......................... C07C 69/76; C07C 69/66
[52] U.S. Cl. .............................................. 560/53; 560/174
[58] Field of Search ...................................... 560/53, 174

[56] References Cited

FOREIGN PATENT DOCUMENTS 2149650 12/1973 Germany .

OTHER PUBLICATIONS

Def. Publ. U.S. Pat Off. Off Gaz U.S.P.T.O. 1971 886(2) 215.
Kabo, T. et al Chem Pharm Bull (1978) 26(12) 3877–9.
Dehmlow, E et al, Liebigs Am Chem (1982) (9) 1753–5.
Abe, Kehue Chem Express (1991) 6(3) 193–6.

*Primary Examiner*—Paul J. Killos
*Attorney, Agent, or Firm*—McAuley Fisher Nissen Goldberg & Kiel

[57] ABSTRACT

Disclosed is a process for the preparation of a 5-hydroxy-3-ketoester derivative of the formula:

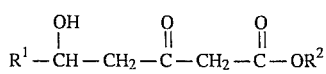

in which $R^1$ represents an alkyl group, an alkenyl group, an alkynyl group, an aryl group or a heterocyclic group, and $R^2$ represents an alkyl group or an aryl group, which comprises causing the reaction of an aldehyde compound of the formula $R^1CHO$ in which $R^1$ has the meanings as defined above and diketene in the presence of a metal compound selected from a titanium or aluminum compound having at least one group of $—OR^3$ in which $R^3$ represents an alkyl group or an aryl group. Further, a process for the preparation of an optically active substance of the 5-hydroxy-3-ketoester derivative causing the reaction of the above compounds in the presence of the metal compound and optically active Schiff base or a complex compound obtained by reacting the metal compound with the optically active Schiff base, also is disclosed.

25 Claims, No Drawings

PROCESS FOR PREPARATION OF 5-HYDROXY-3-KETOESTER DERIVATIVE AND OPTICALLY ACTIVE SUBSTANCE THEREOF

FIELD OF THE INVENTION

The present invention relates to a novel process for the preparation of 5-hydroxy-3-ketoester derivatives and further optically active substances thereof, which are useful as intermediates for preparing blood cholesterol reducing agents [e.g., 4-hydroxy-3-methylglutaric Co-A reductase inhibitor].

BACKGROUND OF THE INVENTION

It is known that 5-hydroxy-3-ketoester derivatives are useful as intermediates for preparing blood cholesterol reducing agent [4-hydroxy-3-methylglutaric (HMG) Co-A reductase inhibitor such as trans-6-[2-(2,4-dichlorophenyl-)ethyl] -3,4,5,6-tetrahydro-4-hydroxy-2H-pyran-2-one].

For example, a process for preparing the above blood cholesterol reducing agent using as the 5-hydroxy-3-ketoester derivative (E)-7-(2,4-dichlorophenyl)-5-hydroxy-3-oxo- 6-heptenoic acid methyl ester is described in Journal of Medicinal Chemistry [J. Med. Chem., 1985, Vol..28, No. 3, pp. 352].

As a process for preparing the 5-hydroxy-3-ketoester derivative, Chemistry Letters [Chem. Lett., pp. 161, 1975] discloses the following process: Aldehydes are reacted with diketene in the presence of $TiCl_4$ at −78° C., which then reacted with alcohols, to prepare the 5-hydroxy-3-ketoester derivative. Further, Chemistry Express [Chem. Express, Vol. 6, No. 3, pp. 193–195, 1991] discloses the process that an aldehyde is reacted with diketene in the presence of samarium triiodide at −45° C., which is then reacted with an alcohol at −10° C., to prepare the 5-hydroxy-3-ketoester derivative.

Thus, these processes are required to perform the reaction at extremely low temperatures (−78° C. or −45° C.), and therefore the processes have disadvantages as industrially applicable processes. Further, these processes are employed for preparing a racemic mixture of the 5-hydroxy- 3-ketoester derivative, while a process for preparing directly an optically active substance of the 5-hydroxy-3-ketoester derivative from aldehyde and diketene has been unknown so far.

SUMMARY OF THE INVENTION

An object of the invention is to provide a novel process which is industrially useful for the preparation of 5-hydroxy-3-ketoester derivatives.

Another object of the invention is to provide a novel process which is industrially useful for the preparation of optically active 5-hydroxy-3-ketoester derivatives.

The invention resides in a process for the preparation of a 5-hydroxy-3-ketoester derivative of the formula (IV):

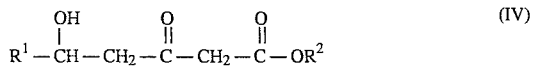

in which $R^1$ represents an alkyl group, an alkyl group having a substituent group, an alkenyl group, an alkenyl group having a substituent group, an alkynyl group, an alkynyl group having a substituent group, an aryl group, an aryl group having a substituent group, a heterocyclic group, or a heterocyclic group having a substituent group, and $R^2$ represents an alkyl group, an alkyl group having a substituent group, an aryl group or an aryl group having a substituent group, which comprises causing the reaction of an aldehyde compound of the formula (I):

$$R^1CHO \qquad (I)$$

in which $R^1$ has the meaning defined above, and diketene of the formula:

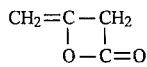

in the presence of a metal compound selected from the group consisting of titanium and aluminum compounds having at least one group of —$OR^3$ in which $R^3$ an alkyl group, an alkyl group having a substituent group, an aryl group or an aryl group having a substituent group;
in which —$OR^2$ is equal to —$OR^3$, or —$OR^2$ is introduced by incorporation of a compound of the —$OR^2$ group into a mixture of the reaction.

Preferred embodiments of the process of the invention are as follow:

1) The process wherein $R^1$ represents an alkyl group of 1 to 12 carbon atoms, an alkyl group of 1 to 12 carbon atoms having a substituent group, an alkenyl group of 2 to 12 carbon atoms or an alkenyl group of 2 to 12 carbon atoms having a substituent group.

2) The process wherein $R^1$ represents an alkyl group of 1 to 12 carbon atoms, an alkyl group of 1 to 12 carbon atoms having an aromatic group (including a heterocyclic group and an aryl group), an alkenyl group of 2 to 12 carbon atoms or an alkenyl group of 2 to 12 carbon atoms having an aromatic group.

3) The process wherein $R^1$ represents an alkenyl group of 2 to 12 carbon atoms having a heterocyclic group (including a heterocyclic ring group having one ring, a fused ring group consisting of two or more heterocyclic rings having one ring and a fused ring group of a heterocyclic ring having one ring and a benzene ring).

4) The process wherein $R^2$ represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms.

5) The process wherein $R^3$ in the metal compound represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms.

6) The process wherein the metal compound is a titanium compound having the formula (II):

$$Ti(OR^3)_n A^1_{4-n} \qquad (II)$$

in which $R^3$ has the meaning defined above, $A^1$ represents a halogen atom or an alkyl group having 1 to 6 carbon atoms (preferably a halogen) and n is an integer of 1 to 4; or an aluminum compound having the formula (III):

$$Al(OR^3)_m A^1{}_{3-m} \qquad (III)$$

in which $R^3$ and $A^1$ have the meanings defined above, and m is an integer of 1 to 3.

7) The process wherein the metal compound is a titanium compound of $Ti(OR^3)_4$ or a aluminum compound of $Al(OR^3)_3$, in which $R^3$ has the meaning defined above.

8) The process wherein $R^2$ is equal to $R^3$ in the metal compound.

9) The process wherein the reaction is performed at a temperature in the range of –40° to 40° C. (prefrably –30 ° to 30° C.).

Further, the present resides in a process for the preparation of an optically active 5-hydroxy-3-ketoester derivative of the formula (VIII):

$$\underset{*}{R^{11}-\overset{OH}{\underset{|}{C}}H} - CH_2 - \overset{O}{\underset{\|}{C}} - CH_2 - \overset{O}{\underset{\|}{C}} - OR^{12} \qquad (VIII)$$

in which $R^{11}$ represents an alkyl group, an alkyl group having a substituent group, an alkenyl group, an alkenyl group having a substituent group, an alkynyl group, an alkynyl group having a substituent group, an aryl group, an aryl group having a substituent group, a heterocyclic group or a heterocyclic group having a substituent group, and $R^{12}$ represents an alkyl group, an alkyl group having a substituent group, an aryl group or aryl group having a substituent group, which comprises causing the reaction of an aldehyde compound of the formula (V):

$$R^{11}CHO \qquad (V)$$

in which $R^{11}$ has the meaning as defined above, and diketene of the formula:

$$\begin{array}{c} CH_2 = C - CH_2 \\ |\phantom{xx} | \\ O - C = O \end{array}$$

in the presence of a metal compound selected from the group consisting of titanium and aluminum compounds having at least one group of —$OR^{13}$ in which $R^{13}$ an alkyl group, an alkyl group having a substituent group, an aryl group or an aryl group having a substituent group and optically active Schiff base, or a complex compound obtained by reacting the metal compound with the optically active Schiff base;

wherein —$OR^{12}$ is equal to —$OR^{13}$ or —$OR^{12}$ is introduced by incorporation of a compound of the —$OR^{12}$ group into a mixture of the reaction.

Preferred embodiments of the process of the invention are as follow:

1) The process wherein wherein $R^{11}$ represents an alkyl group of 1 to 12 carbon atoms, an alkyl group of 1 to 12 carbon atoms having a substituent group, an alkenyl group of 2 to 12 carbon atoms or an alkenyl group of 2 to 12 carbon atoms having a substituent group.

2) The process wherein wherein $R^{11}$ represents an alkyl group of 1 to 12 carbon atoms, an alkyl group of 1 to 12 carbon atoms having an aromatic group (including a heterocyclic group and an aryl group), an alkenyl group of 2 to 12 carbon atoms or an alkenyl group of 2 to 12 carbon atoms having an aromatic group.

3) The process wherein wherein $R^{11}$ in the formula (V) and the formula (VIII) represents an alkenyl group of 2 to 12 carbon atoms having a heterocyclic group (including a heterocyclic ring group having one ring, a fused ring group consisting of two or more heterocyclic rings having one ring and a fused ring group of a heterocyclic ring having one ring and a benzene ring).

4) The process wherein $R^{12}$ represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms.

5) The process wherein $R^{13}$ represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms.

6) The process wherein the metal compound is a titanium compound having the formula (VI):

$$Ti(OR^{13})_p A^2{}_{4-p} \qquad (VI)$$

in which $R^{13}$ has the meanings as defined above 11, $A^2$ represents a halogen atom or an alkyl group having 1 to 6 carbon atoms (preferably a halogen) and p is an integer of 1 to 4 (preferably 3 or 4); or an aluminum compound having the formula (VII):

$$Al(OR^{13})_q A^2{}_{3-q} \qquad (VII)$$

in which $R^{13}$ and $A^2$ have the meanings defined above, and m is an integer of 1 to 3.

7) The process wherein the metal compound is a titanium compound of $Ti(OR^{13})_4$ in which $R^{13}$ has the meaning defined above.

8) The process wherein $R^{12}$ is equal to $R^{13}$ of the metal compound.

9) The process wherein the optically active Schiff base has the formula (IX):

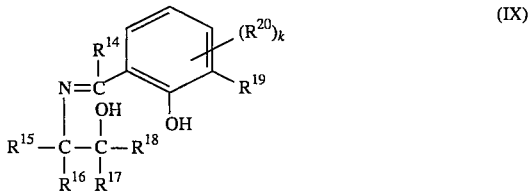

in which each of $R^{14}$, $R^{15}$, $R^{16}$, $R^{17}$, $R^{18}$ and $R^{19}$ represents a hydrogen atom, an alkyl group, an aryl group or an aralkyl group, $R^{20}$ represents a hydrogen atom, an alkyl group, an aralkyl group, an alkyloxy group, an aryloxy group, a halogen atom, a nitro group, an alkyloxycarbonyl group, an aryloxycarbonyl group, a cyano group or an acyloxy group, and k represents an integer of 1 to 3, at least one of a carbon atom bonding to $R^{15}$ and $R^{16}$ and a carbon atom bonding to $R^{17}$ and $R^{18}$ being an asymmetric carbon atom.

10) The process 9) wherein each of $R^{14}$ and $R^{16}$ represents a hydrogen atom, $R^{15}$ represents a hydrogen atom, an alkyl group or phenyl group and each of $R^{13}$, $R^{17}$, $R^{18}$, $R^{19}$ and $R^{20}$ represents a hydrogen atom or an alkyl group.

11) The process wherein the reaction is performed in the presence of the complex compound of the metal compound and the optically active Schiff base.

12) The process wherein the reaction is performed after the complex compound of the metal compound and the optically active Schiff base form together a complex compound.

13) The process wherein the reaction is performed at a temperature in the range of −40° to 40° C.

DETAILED DESCRIPTION OF THE INVENTION

The process for the preparation of the 5-hydroxy-3-ketoester derivative of the formula (IV) according to the invention is explained below.

The derivative (IV) can be prepared by causing the reaction of an aldehyde compound of the formula (I) and diketene in the presence of a metal compound selected from titanium and aluminum compounds having an alkoxy group or aryloxy, or an alkoxy group or aryloxy having a substituent group.

$R^1$ of the formula (I) representing the aldehyde compound is an alkyl group, an alkenyl group, an alkynyl group, an aryl group or a heterocyclic group; or an alkyl group, an alkenyl group, an alkynyl group, an aryl group or a heterocyclic group, each of which has a substituent group.

Examples of the alkyl group include a chain alkyl group and a cycloalkyl group.

The cycloalkyl group preferably is cycloalkyl of 3–12 carbon atoms (more preferably 3–10 carbon atoms). Preferred examples of the cycloalkyl of 3–10 carbon atoms are cyclopropyl, cyclobutyl, cyclopentyl and cyclohexyl.

The chain alkyl group preferably is alkyl of 1–12 carbon atoms (more preferably 1–10 carbon atoms). Preferred examples of alkyl of 1–10 carbon atoms include methyl, ethyl, propyl and its isomer (i.e., isopropyl), butyl and its isomers, and pentyl and its isomers.

Examples of substituent groups of the chain alkyl group include an aryl group such as phenyl and aryl groups substituted with at least one group of alkyl of 1–5 carbon atoms, alkoxy of 1–5 carbon atoms, phenyl, fluorophenyl, alkylphenyl of 7–12 carbon atoms and halogen such as 4-tolyl, 4-chlorophenyl, 4-methoxyphenyl, 3,5-dichloro-6-(4-fluorophenyl)phenyl, 2,4-dichlorophenyl and 2,4-dimethyl-6-( 4-fluoro-3-methylphenyl)phenyl; and heterocyclic groups and heterocyclic groups having a substituent group substituted with at least one group of alkyl of 1–5 carbon atoms, alkoxy of 1–5 carbon atoms, alkoxycarbonyl of 2–6 carbon atoms, phenyl, fluorophenyl, alkylphenyl of 7–12 carbon atoms, benzyloxycarbonyl, cycloalkyl of 1–6 carbon atoms, N-methyl-N-methanesulfonyl)amino and halogen, such as:

an indolyl group (e.g., indolyl) and indolyl groups substituted with at least one group of alkyl of 1–5 carbon atoms, fluorophenyl and halogen (e.g., 3-(4-fluorophenyl)- 1-isopropylindol-2-yl);

a pyridyl group (e.g., pyridyl) and pyridyl groups substituted with at least one group of alkyl of 1–5 carbon atoms, alkoxy of 1–5 carbon atoms, alkoxycarbonyl of 2–6 carbon atoms, phenyl, fluorophenyl, alkylphenyl of 7–12 carbon atoms, benzyloxycarbonyl and halogen (e.g., 4-phenyl-2-methylpyridin-3-yl, 2-isopropyl-6-phenyl-4-(4-fluorophenyl)pyridin- 3-yl, 2,5-diisopropyl-4-(4-fluorophenyl)pyridin- 3-yl, 2,6-diisopropyl-4-(4-fluorophenyl)-5-benzyloxymethylpyridin- 3-yl and 2,6-diisopropyl-4-(4-fluorophenyl)- 5-ethoxycarbonylpyridin-3-yl);

a pyrimidyl group (e.g., pyrimidyl) and pyrimidyl groups substituted with at least one group of alkyl of 1–5 carbon atoms, phenyl, fluorophenyl, N-methyl-N-methanesulfonyl)-amino and halogen (e.g., 6-isopropyl-2-phenyl-4-(4-fluorophenyl)pyrimidin- 5-yl, 6-methyl-2-phenyl-4-(4-fluorophenyl)pyrimidin- 5-yl, 2,4-dimethyl-6-(4-fluorophenyl)pyrimidin- 5-yl and 2-(N-methyl-N-methanesulfonyl)amino-6-( 4-fluorophenyl)-4-isopropylpyrimidin-5-yl);

a quinolyl group (e.g., quinolyl) and quinolyl groups substituted with at least one group of alkyl of 1–5 carbon atoms, cycloalkyl of 1–6 carbon atoms, fluorophenyl and halogen (e.g., quinolyl, 3-isopropyl-1-(4-fluorophenyl)-4-oxoquinolin- 2-yl and 2-cyclopropyl-4-(4-fluorophenyl)-quinolin- 3-yl);

a pyrazolyl group (e.g., pyrazolyl) and a pyrazolyl group substituted with at least one group of alkyl of 1–5 carbon atoms, phenyl, fluorophenyl and halogen (e.g., 5-(4-fluorophenyl)- 3-isopropyl-1-phenylpyrazol-4-yl);

a pyridazinyl group (e.g., pyridazinyl) and a pyridazinyl group substituted with at least one group of alkyl of 1–5 carbon atoms, fluorophenyl and halogen (e.g., 3,4-bis( 4-fluorophenyl)-6-isopropylpyridazin-5-yl);

an imidazolyl group (e.g., imidazolyl) and an imidazolyl group substituted with at least one group of alkyl of 1–5 carbon atoms, phenyl, fluorophenyl and halogen (e.g., 4-isopropyl-2-phenyl-1-(4-fluorophenyl)-1H-imidazol-5-yl);

a pyrrolyl group (e.g., pyrrolyl) and pyrrolyl groups substituted with at least one group of alkyl of 1–5 carbon atoms, phenyl, fluorophenyl and halogen (e.g., 2-isopropyl-1-phenyl-4-(4-fluorophenyl)pyrrol-3-yl and 1-isopropyl-3, 4-bis( 4-fluorophenyl)pyrrole-2,5-diyl);

an imidazoline-2-one group (e.g., imidazoline-2-one) and an imidazoline-2-one group substituted with at least one group of alkyl of 1–5 carbon atoms, phenyl, fluorophenyl and halogen (e.g., 4-(4-fluorophenyl)-1-methyl-3-phenylimidazol- 2-on-5-yl);

a furyl group; a benzofuryl group; a thiazolyl group, a benzthiazolyl; and a thioenyl group.

The alkenyl group preferably is alkenyl of 2–12 carbon atoms (more preferably 2–10 carbon atoms). Preferred examples of the alkenyl of 2–12 carbon atoms are vinyl, propenyl and its isomer (i.e., isopropenyl) and butenyl and its isomers.

The alkynyl group preferably is alkynyl of 2–12 carbon atoms (more preferably 2–10 carbon atoms). Preferred examples of the alkynyl of 2–12 carbon atoms are ethynyl, propynyl and its isomer (i.e., 2-propyn-1-yl and 1-propyn-1-yl), and butynyl and its isomers.

Examples of substituent groups of the alkenyl group and the alkynyl group include those of the substituent groups of the alkyl group as mentioned above. Further, examples of the substituent groups include a vinyl group such as vinyl and vinyl groups substituted with at least one group of alkyl of 1–5 carbon atoms, phenyl, fluorophenyl, tetrazole and halogen; such as 1-phenylethenyl, 2,2-diphenylethenyl, 1-isopropyl-2,2-bis(4-fluorophenyl)ethenyl and 1-(1-methyl-1H-tetrazol-5-yl)-2,2-bis(4-fluorophenyl)ethenyl; and an ethynyl group such as ethynyl and ethynyl groups substituted with at least one group of alkoxyphenyl of 7–12 carbon atoms, phenyl, chlorophenyl and halogen such as 4-chlorophenylethynyl and 4-methoxyphenylethynyl.

The number and position of the substituent are not particularly restricted.

Preferred examples of the alkyl groups having a substituent group include:

benzyl, phenethyl, 3-phenylpropyl and 4-phenylbutyl.

Preferred examples of the alkenyl groups having a substituent group include:

styryl, cinnamyl, 2-(4-tolyl)ethenyl, 2-(4-chlorophenyl)ethenyl, 2-(4-methoxyphenyl)ethenyl, 2-[3,5-dichloro-6-(4-fluorophenyl)phenyl]ethenyl and 2-[2,4-dimethyl-6-(4-fluoro-3-methylphenyl)phenyl]ethenyl;

2-(indol-2-yl)ethenyl and 2-[3-(4-fluorophenyl)-1-isopropylindol- 2-yl]ethenyl;

2-(pyridin-3-yl)ethenyl, 2-(2-methyl-4-phenylpyridin-3-yl)ethenyl, 2-[2-isopropyl-6-phenyl-4-(4-fluorophenyl)pyridin- 3-yl]ethenyl, 2-[2,5-diisopropyl-4-(4-fluorophenyl)pyridin- 3-yl]ethenyl, 2-[2,6-diisopropyl-4-(4-fluorophenyl)- 5-benzyloxymethylpyridin-3-yl]ethenyl, and 2-[2,6-diisopropyl- 4-(4-fluorophenyl)-5-ethoxycarbonylpyridin-3-yl] ethenyl;

2-(pyrimidin-5-yl)ethenyl, 2-[6-isopropyl-2-phenyl-4-(4-fluorophenyl)pyrimidin-5-yl]ethenyl, 2-[6-methyl-2-phenyl- 4-(4-fluorophenyl)pyrimidin-5-yl]ethenyl, 2-[2,4-dimethyl- 6-(4-fluorophenyl)pyrimidin-5-yl]ethenyl and 2-[2-(N-methyl-N-methanesulfonyl)amino- 6-(4-fluorophenyl)-4-isopropylpyrimidin- 5-yl]ethenyl;

2-(quinolin-3-yl)ethenyl and 2-[cyclopropyl-4-(4-fluorophenyl)quinolin- 3-yl]ethenyl;

2-(quinolin-2-yl)ethenyl and 2-[1-(4-fluorophenyl)-3-isopropyl- 4-oxoquinolin-2-yl]ethenyl;

2-(pyrazol-4-yl)ethenyl and 2-[5-(4-fluorophenyl)-3-isopropyl- 1-phenylpyrazol-4-yl]ethenyl;

2-(pyridazin-5-yl)ethenyl and 2-[3,4-bis(4-fluorophenyl)-6-isopropylpyridazin-5-yl]ethenyl;

2-(imidazol-5-yl) -ethenyl and 2-[4-isopropyl-2-phenyl-1- (4-fluorophenyl) -1H-imidazol-5-yl] ethenyl;

2-(pyrrol-3-yl)ethenyl and 2-[4-(4-fluorophenyl)-2-isopropyl- 1-phenyl-pyrrol-3-yl]ethenyl;

2-(imidazolin-2-on-5-yl)ethenyl and 2-[4-(4-fluorophenyl)- 1-methyl-3-phenylimidazol-2-on-5-yl]ethenyl;

2-(furan-2-yl)ethenyl; and 2-(thiophen-2-yl)ethenyl.

Preferred examples of the alkynyl groups include:

2-phenylethynyl, 3-phenyl-2-propynyl and 4-phenyl-3-butyn- 1-yl.

The aryl group represented by $R^1$ generally is a phenyl group and a naphthyl group which have a substituent group, and those which have no substituent groups.

The substituent of the phenyl group or the naphthyl group generally is halogen, alkyl of 1–10 carbon atoms, alkoxy of 1–10 carbon atoms, nitro, cyano and phenyl. Preferred examples of the substituent include fluorine, chlorine, bromine, iodine, methyl, ethyl, propyl and its isomers, butyl and its isomers, pentyl and its isomers, methoxy, ethoxy, propoxy and its isomers, butoxy and its isomers, nitro, cyano and phenyl. The number and position of the substituent are not particularly restricted.

The heterocyclic group represented by $R^1$ may have a substituent or may have no substituents.

Examples of the heterocyclic groups include furyl, benzofuryl, thienyl, pyrrolyl, pyridyl, pyrimidyl, piperidyl, morpholinyl, quinolyl, thiazolyl, benzothiazolyl, imidazolyl and triazolyl. Preferred examples include furyl, thienyl, pyrrolyl, pyridyl, pyrimidyl, quinolyl and triazolyl.

The substituent group of the heterocyclic group generally is halogen, alkyl of 1–10 carbon atoms, alkoxy of 1–10 carbon atoms, nitro, cyano and phenyl. Preferred examples of the substituent include fluorine, chlorine, bromine, iodine, methyl, ethyl, propyl and its isomers, butyl and its isomers, methoxy, ethoxy, propoxy and its isomers, butoxy and its isomers, nitro, cyano and phenyl. The number and position of the substituent are not particularly restricted.

$R^1$ preferably represents an alkyl group of 1 to 12 carbon atoms, an alkyl group of 1 to 12 carbon atoms having a substituent group (preferalby an aromatic group including an aryl group and a heterocyclic group, and specifically a heterocyclic group), an alkenyl group of 2 to 12 carbon atoms or an alkenyl group of 2 to 12 carbon atoms having a substituent group (preferalby an aromatic group, and more preferably a heterocyclic group). $R^1$ specifically represents an alkenyl group of 2 to 12 carbon atoms having a heterocyclic group. The heterocyclic group includes a group of a heterocyclic ring having one ring, a group of a fused ring consisting of two or more heterocyclic rings having one ring and a group of a fused ring of a heterocyclic ring having one ring and a benzene ring. Further, the heterocyclic group preferably is a group of pyridine or a group of a fused ring having pyridine (e.g., quinoline and isoquinoline).

The metal compounds employed in the reaction of the invention are titanium compounds having at least one group of —$OR^3$ and aluminum compounds having at least one group of —$OR^3$. $R^3$ represents an alkyl group, an alkyl group, an aryl group or an aryl group. The metal compound may have a halogen atom or an alkyl group other than the above group of (—$OR^3$).

$R^3$ in the metal compound preferably represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms. $R^3$ more preferably is phenyl or alkyl of 1–10 carbon atoms, and more preferably phenyl, methyl, ethyl, propyl and its isomers, butyl and its isomers or pentyl and its isomers.

The metal compound preferably is a titanium compound having the formula (II):

$$Ti(OR^3)_n A^1_{4-n} \quad (II)$$

in which $R^3$ has the meanings as defined above, $A^1$ represents a halogen atom or an alkyl group having 1 to 6 carbon atoms (preferably a halogen) and n is an integer of 1 to 4; or an aluminum compound having the formula (III):

$$Al(OR^3)_m A^1_{3-m} \quad (III)$$

in which $R^3$ and $A^1$ have the meanings as defined above, and m is an integer of 1 to 3.

At least one of prural $R^3$ of the titanium compound and the aluminum compound preferably represents an alkyl group.

The metal compound can be $Ti(OR^3)_4$, $Ti(OR^3)_3 A^1$, $Ti(OR^3)_2 A^1_2$, $Al(OR^3)_3$, or $Al(OR^3)_2 A^1$, preferably $Ti(OR^3)_4$, $Ti(OR^3)_3 A^1$, $Al(OR^3)_3$, or $Al(OR^3)_2 A^1$, and specifically is $Ti(OR^3)_4$ or $Al(OR^3)_3$.

In the invention, $R^3$ is equal to $R^2$ of the formula (IX) (5-hydroxy-3-ketoester derivative), or —$OR^2$ of the formula is introduced by incorporation of a compound having the —$OR^2$ group into a mixture of the reaction. In more detail, in the case that the reaction is performed using only the aldehyde, diketene and the metal compound with no solvent or together with a compound (solvent) having no —$OR^2$, $R^3$ is generally equal to $R^2$. However, in the case that the reaction is performed using the aldehyde, diketene, the metal compound and a compound (solvent) having —$OR^2$, $R^3$ is not introduced in 5-hydroxy-3-ketoester derivative of the formula (IV), or partially introduced in the derivative. The compound having —$OR^2$ may be added to the reaction mixture (aldehyde, diketene and metal compound), or may be added to the reaction mixture while the reaction proceeds or after the reaction is complete.

Examples of the compounds having —$OR^2$ include alcohols such as methanol, ethanol, propanol and its isomer, butanol and its isomers, and pentanol and its isomers; and esters such as methyl acetate, ethyl acetate, n-propyl acetate, butyl acetate, isobutyl acetate, t-butyl acetate, isoamyl acetate and methyl propionate.

The 5-hydroxy-3-ketoester derivative of the formula (IV) is obtained by causing the reaction of an aldehyde compound of the formula (I) $R^1CHO$ and diketene in the presence of a metal compound selected from titanium and aluminum compounds having —$OR^3$ (an alkoxy group, aryloxy or an alkoxy group or aryloxy having a substituent group). Therefore, $R^1$ of the formula (IV) is restricted by those of the formula (I) and $R^2$ of the formula (IV) is restricted by the metal compound having —$OR^3$ and the compound (solvent) having —$OR^2$ employed in the reaction.

The process of the invention is, for example, conducted according to the following reaction scheme:

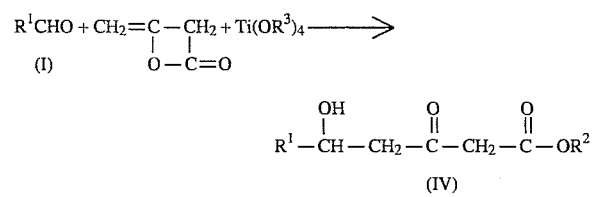

Although $Ti(OR^3)_4$ is employed as the metal compound in the above reaction formula, other metal compounds as mentioned above may be employed.

In the process, the aldehyde compound of the formula (I), diketene and the metal compound may be added in any order to a reaction system. Further, these compounds may be added in the forms of their solutions obtained by dissolving them in a solvent described later.

The ratio between the aldehyde compound of the formula (I) and the diketene generally is in the range of 1:0.5– 1:4.0 ((I):diketene; molar ratio), preferably 1:0.7– 1:3.0, and more preferably 1:0.8–1:2.5.

The ratio between the aldehyde compound of the formula (I) and the metal compound generally is in the range of 1:0.5–1:4.0 ((I):metal; molar ratio), preferably 1:0.7– 1:3.0, and more preferably 1:0.8–1:2.5.

The diketene and most of the metal compounds are in the form of liquid at room temperature, and therefore they can be used with no solvent. In this case, the aldehyde compound is employed by dissolving in (or mixing with) these compounds. These compounds and the aldehyde compound also can be used in the form of a solution in an organic solvent. This solution can be prepared by dissolving these compounds in an organic solvent. Any organic solvents can be used, provided that they do not participate in the reaction.

Examples of the employable organic solvents include alkyl halides such as methylene chloride and chloroform, aromatic hydrocarbons such as benzene, toluene and xylene, aliphatic hydrocarbons such as pentane, hexane and heptane, ethers such as diethyl ether, diisopropyl ether and tetrahydrofuran (THF), nitriles such as acetonitrile and propionitrile, alcohols such as compounds described in the examples of the compounds having —$OR^2$, and esters such as compounds described in the examples of the compounds having —$OR^2$. Preferred are ethyl acetate, methylene chloride, isopropyl ether, and toluene.

The solvent generally is used in the amount of 0.01%– 100% (by weight), preferably 0.1%–50% and more preferably 1%–20% based on the amount of the aldehyde compound of the formula (I).

The mixture of the aldehyde compound, the diketene and the metal compound (the organic solvent, if desired) is caused to react at a temperature in the range of –78° C. to 50° C., generally in the range of –60° C. to 50° C., preferably in the range of –40° C. to 40° C., and more preferably in the range of –30° C. to 30° C. and most preferably in the range of –25° C. to 25° C.

The reaction period preferably is in the range of 1–100 hours, and more preferably in 10–60 hours.

After completion of the above reaction, the resulting reaction mixture containing the 5-hydroxy-3-ketoester derivative is generally subjected to isolation procedure. For example, a dilute acidic aqueous solution is added to the mixture to make the mixture acidic with stirring, and then an organic solvent is added to the acidic mixture to extract the 5-hydroxy-3-ketoester derivative. The extract is then dried and concentrated in vacuo to obtain the derivative. The derivative can be further purified by distillation or by the use of silica gel chromatography.

Preferred examples of the mineral acid for the use in the isolation procedure include hydrochloric acid and sulfuric acid, and hydrochloric acid is most preferred. The concentration of the acidic solution generally is in the range of 0.05N–10N, preferably in the range of 0.1N–10N and more preferably in the range of 0.3N–2.0N. The acidic solution is generally used in 0.5–20 times volume of the reaction mixture, and preferably in 0.7–10 times volume in the case of using 1N-HCl.

The process for the preparation of the optically active 5-hydroxy-3-ketoester derivative of the formula (VIII) (i.e., the optically active substance of the 5-hydroxy- 3-ketoester derivative of the formula (IV)) according to the invention is explained below.

The derivative can be prepared by causing the reaction of an aldehyde compound of the formula (V) $R^{11}CHO$, diketene and a metal compound selected from titanium and aluminum compounds having —$OR^{13}$ (an alkoxy group, aryloxy or aralkyloxy) in the presence of an optically active Schiff base.

$R^{11}$ of the formula (V) representing the aldehyde compound stands for the same groups as those represented by $R^1$ of the formula (I). Diketene is also the same as one used in the preparation of the 5-hydroxy-3-ketoester derivative of the formula (IV). Further, as material of the metal compound, the compounds used in the process can be used. However, the optically active Schiff base is employed only in this reaction.

As the optically active Schiff base, any schiff base can be employed so long as it has an optical activity. The optically active Schiff base preferably has the formula (IX):

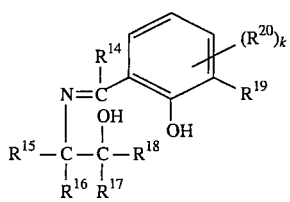

(IX)

in which each of $R^{14}$, $R^{15}$, $R^{16}$, $R^{17}$, $R^{18}$ and $R^{19}$ represents a hydrogen atom, an alkyl group, an aryl group or an aralkyl group, $R^{20}$ represents a hydrogen atom, an alkyl group, an aralkyl group, an alkyloxy group, an aryloxy group, a halogen atom, a nitro group, an alkyloxycarbonyl group, an aryloxycarbonyl group, a cyano group or an acyloxy group, and k represents an integer of 1 to 3, at least one of a carbon atom bonding to $R^{15}$ and $R^{16}$ and a carbon atom bonding to $R^{17}$ and $R^{18}$ being an asymmetric carbon atom.

$R^{15}$ preferably is hydrogen, phenyl or alkyl of 1–10 carbon atoms, more preferably hydrogen, phenyl, methyl, propyl and its isomer, butyl and its isomers, and pentyl and its isomers, most preferably methyl, propyl and its isomer, and butyl and its isomers.

Each of $R^{17}$ and $R^{18}$ preferably is hydrogen, phenyl or alkyl of 1–10 carbon atoms, more preferably hydrogen, phenyl, methyl, propyl and its isomer, butyl and its isomers, and pentyl and its isomers, most preferably hydrogen.

$R^{19}$ of the formula (IX) generally is hydrogen, phenyl or alkyl of 1–10 carbon atoms, preferably hydrogen, phenyl, methyl, propyl and its isomer, butyl and its isomers, and pentyl and its isomers, and more preferably butyl and its isomers.

Each of $R^{14}$ and $R^{16}$ preferably is hydrogen.

$R^{20}$ of the formula (IX) generally is hydrogen, phenyl or alkyl of 1–10 carbon atoms, preferably hydrogen, phenyl, methyl, propyl and its isomer, butyl and its isomers, and pentyl and its isomers, more preferably hydrogen or butyl and its isomers and most preferably hydrogen. "k" generally is 1 or 2, and preferably 1.

In the formula (IX), it is particularly preferred that each of $R^{14}$ and $R^{16}$ represents a hydrogen atom, $R^{15}$ represents a hydrogen atom, an alkyl group or phenyl group and each of $R^{13}$, $R^{17}$, $R^{18}$, $R^{19}$ and $R^{20}$ represents a hydrogen atom or an alkyl group.

The metal compounds employed in the preparation of the optically active 5-hydroxy-3-ketoester derivative of the formula (VIII) are titanium compounds having at least one group of —$OR^{13}$ and aluminum compounds having at least one group of —$OR^{13}$. $R^{13}$ represents an alkyl group, an alkyl group, an aryl group or an aryl group. The metal compound may be have a halogen atom or an alkyl group other than the above group of (—$OR^{13}$).

$R^{13}$ of the metal compound preferably represents an alkyl group of 1 to 12 carbon atoms, an aryl group of 6 to 15 carbon atoms, an alkyl group of 7 to 20 carbon atoms having an aryl group, an aryl group of 6 to 15 carbon atoms having at least one substituent group selected from the group consisting of halogen, cyano, nitro and alkyl of 1 to 6 carbon atoms, or an alkyl group of 7 to 20 carbon atoms having an aryl group which is substituted with at least one substituent group selected from the group consisting of halogen, cyano, nitro and alkyl of 1 to 6 carbon atoms. $R^{13}$ more preferably is phenyl or alkyl of 1–10 carbon atoms, and more preferably phenyl, methyl, ethyl, propyl and its isomers, butyl and its isomers, or pentyl and its isomers.

The metal compound preferably is a titanium compound having the formula (VI):

$$Ti(OR^{13})_p A^2_{4-p} \quad (VI)$$

in which $R^{13}$ has the meanings as defined above, $A^2$ represents a halogen atom or an alkyl group having 1 to 6 carbon atoms (preferably a halogen) and p is an integer of 1 to 4 (preferably 3 or 4); or an aluminum compound having the formula (VII):

$$Al(OR^{13})_q A^2_{3-q} \quad (VII)$$

in which $R^{13}$ and $A^2$ have the meanings as defined above, and m is an integer of 1 to 3.

At least one of prural $R^{13}$ of the titanium compound and the aluminum compound preferably represents an alkyl group.

The metal compound more preferably is $Ti(OR^{13})_4$, $Ti(OR^{13})_3 A^2$ or $Ti(OR^{13})_2 A^2_2$, and most preferably is $Ti(OR^{13})_4$.

In the invention, $R^{13}$ is equal to $R^{12}$ in the formula (IX) (5-hydroxy-3-ketoester derivative), or —$OR^{12}$ in the formula is introduced by incorporation of a compound having the —$OR^{12}$ group into a mixture of the reaction. In more detail, in the case that the reaction is performed using only the aldehyde, diketene and the metal compound with no solvent or together with a compound (solvent) having no —$OR^{12}$, $R^{13}$ is generally equal to $R^{12}$. However, in the case that the reaction is performed using the aldehyde, diketene, the metal compound and a compound (solvent) having —$OR^{12}$, $R^{13}$ is not introduced in 5-hydroxy-3-ketoester derivative of the formula (VIII) or partially introduced in the derivative. The compound having —$OR^{12}$ may be added to the reaction mixture (aldehyde, diketene and metal compound), or may be added to the reaction mixture that the reaction is conducted for a desired time period.

Examples of the compounds having —$OR^{12}$ include alcohols such as methanol, ethanol, propanol and its isomer, butanol and its isomers, and pentanol and its isomers; and esters such as methyl acetate, ethyl acetate, n-propyl acetate, butyl acetate, isobutyl acetate, t-butyl acetate, isoamyl acetate, and methyl propionate.

The optically active 5-hydroxy-3-ketoester derivative of the formula (VIII) can be obtained by causing the reaction of an aldehyde compound of the formula (V) (namely, $R^{11}CHO$), diketene and a metal compound selected from titanium and aluminum compounds having —$OR^{12}$ (an alkoxy group, aryloxy or aralkyloxy) in the presence of an optically active Schiff base. Therefore, $R^{11}$ of the formula (VIII) is restricted by those of the formula (V), and $R^{12}$ of the formula (IV) is restricted by the metal compound having —$OR^{13}$ and the compound (solvent) having —$OR^{12}$ employed in the reaction.

The process of the invention is, for example, conducted according to the following reaction scheme:

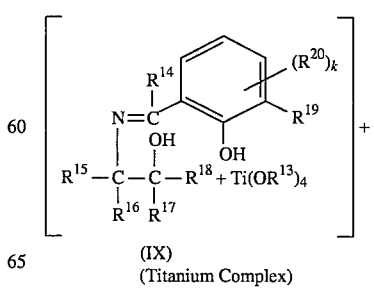

(IX)
(Titanium Complex)

-continued

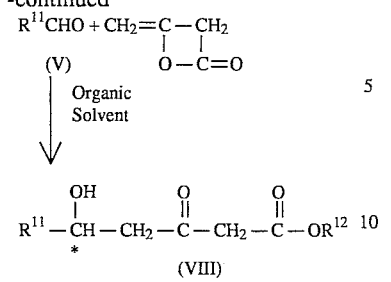

Although Ti(OR$^{13}$)$_4$ is employed as the metal compound and the compound of the formula (IX) is used as the optically active Schiff base in the above reaction formula, other compounds as mentioned above may be employed.

The optically active Schiff base is usually caused to react with the metal compound to form their complex. In the reaction, an organic solvent is not generally employed. The reaction is described in Journal of Organic Chemistry (J. Org. Chem., Vol. 58, pp. 1515, 1993). For example, the schiff base of the formula (IX) can be prepared according the above Journal of Organic Chemistry, by causing the reaction between the following two compounds (hydroxy-aldehyde derivative and optically active β-aminoalcohol).

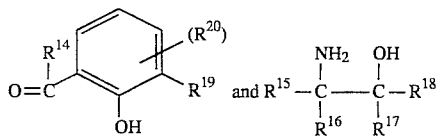

($R^{14}$, $R^{15}$, $R^{16}$, $R^{17}$, $R^{18}$, $R^{19}$, $R^{20}$ and k have meanings as defined in the formula (IX))

Subsequently, the aldehyde compound of the formula (V) and diketene are added to the complex. The aldehyde compound and diketene may be used with no solvent, or they may be used in the form of a solution obtained by dissolving in an organic solvent.

The ratio between the Schiff base and the metal compound generally is in the range of 1:0.8–1:1.2 (Schiff:metal; molar ratio), and preferably 1:0.85– 1:1.15.

The ratio between the Schiff base and the aldehyde compound generally is in the range of 1:0.2–1:10 (Schiff:aldehyde; molar ratio), and preferably 1:0.5–1:5.

The ratio between the Schiff base and the diketene generally is in the range of 1:0.1–1:15 (Schiff:diketene; molar ratio), and preferably 1:0.2–1:10.

As the organic solvents, any organic solvents can be used, provided that they do not participate in the reaction. Examples of the employable organic solvents include alkyl halides such as methylene chloride and chloroform, aromatic hydrocarbons such as benzene, toluene and xylene, aliphatic hydrocarbons such as pentane, hexane and heptane, ethers such as diethyl ether, diisopropyl ether and tetrahydrofuran (THF), nitriles such as acetonitrile and propionitrile, alcohols such as compounds described in the examples of the compounds having —OR$^{12}$, and esters such as compounds described in the examples of the compounds having —OR$^{12}$. Preferred are ethyl acetate, methylene chloride, isopropyl ether, and toluene.

The solvent generally is used in 0.01–100 times volume of the Schiff base, preferably in 1–50 times volume, more preferably in 1–20 times volume.

The mixture of the aldehyde compound, the diketene and the metal compound (the organic solvent if desired) is caused to react at a temperature in the range of –40° C. to 40° C., and more preferably in the range of –30° C. to 30° C. and most preferably in the range of –25° C. to 25° C.

The reaction period preferably is in the range of 1–100 hours, and more preferably in 10–60 hours.

The reaction generally is performed under an inert atmosphere such as $N_2$ gas, He gas and Ar gas, and preferably under an atmosphere of $N_2$ gas or Ar gas.

After completion of the above reaction, the resulting reaction mixture containing the optically active 5-hydroxy-3-ketoester derivative is generally subjected to isolation procedure. For example, a dilute acidic aqueous solution is added to the mixture to make the mixture acidic with stirring, and then an organic solvent is added to the acidic mixture to extract the optically active 5-hydoroxy- 3-ketoester derivative. The extract is then dried and concentrated in vacuo to obtain the derivative. The derivative is further purified by distillation or by the use of silica gel chromatography.

Preferred examples of the mineral acid in the isolation operation include hydrochloric acid and sulfuric acid, and hydrochloric acid is most preferred. The concentration of the acidic solution generally is in the range of 0.05N–10N, preferably in the range of 0.1N–10N and more preferably in the range of 0.3N–2.0N. The acidic solution is generally used in 1–50 times volume of the reaction mixture, and preferably in 2–25 times volume in the case of 1N-HCl.

The present invention is further illustrated by the following examples, but those examples are given by no means to restrict the invention.

In the first place, the examples 1–7 showing the process for the preparation of 5-hydroxy-3-ketoester derivative of the formula (IV) are described below.

EXAMPLE 1

In an atmosphere of argon, 10 ml of dichloromethane and 2.8 ml (9.43 mmol (millimole)) of titanium tetraisopropoxide were placed in a schlenk tube, and cooled to 0° C. with stirring. To the dichloromethane solution, 0.96 ml (9.42 mmol) of benzaldehyde and 1.5 ml (18.8 mmol) of diketene were added, and vigorously stirred at 0° C. over 25 hours to give a reaction mixture. The reaction mixture was added to a mixed solution of 50 ml of 1N HCl and 50 ml of diethyl ether, and vigorously stirred at room temperature over 24 hours to give a solution. The solution was extracted with three portions of 50 ml of diethyl ether. The diethyl ether portions were combined, washed twice with 50 ml of a saturated sodium hydrogen carbonate aqueous solution, and further washed twice with 50 ml of a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of hexane and ethyl acetate (hexane:ethyl acetate= 5:1) to give 1.74 g of isopropyl 5-hydroxy- 3-oxo-5-phenylpentanoate (yield: 74% based on the amount of benzaldehyde).

IR-spectra $\gamma_{max}$ (neat)
3508, 2984, 2936, 1746, 1646, 1314, 1106 (cm$^{-1}$)
$^1$H-NMR(CDCl$_3$, 250 MHz) δ:
1.26 (d, J=6.7 Hz, 6H), 2.4 (brs, 1H),
2.94 (d, J=3.7 Hz, 1H) , 2.97 (d, J=9.2 Hz, 1H) ,
3.46 (s, 2H), 5.0–5.1 (m, 1H),
5.2 (dd, J=3.7 Hz, 9.2 Hz, 1H), 7.3–7.4 (m, 5H)

EXAMPLE 2

In an atmosphere of argon, 50 ml of dichloromethane and 25.8 g (0.091 mol) of titanium tetraisopropoxide were placed in a schlenk tube, and cooled to 0° C. with stirring. To the dichloromethane solution, 10 g (0.076 mol) of E-cinnamaldehyde and 13.2 g (0.152 mol) of diketene were added, and vigorously stirred at 0° C. over 25 hours to obtain a reaction mixture. The reaction mixture was added to a mixed solution of 50 ml of 1N HCl and 50 ml of diethyl ether, and vigorously stirred at room temperature over 15 hours to give a solution. The solution was extracted with three portions of 250 ml of diethyl ether. The diethyl ether portions were combined, washed twice with 50 ml of a saturated sodium hydrogen carbonate aqueous solution, and further washed twice with 50 ml of a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of hexane and ethyl acetate (hexane:ethyl acetate= 5:1) to give 18.5 g of isopropyl 5-hydroxy-3-oxo-7-phenyl-6-heptanoate (yield: 89% based on the amount of E-cinnamaldehyde).

IR-spectra $\gamma_{max}$ (neat):
3472, 2984, 2936, 1716, 1314, 1106 (cm$^{-1}$)
$^1$H-NMR(CDCl$_3$, 250 MHz) δ:
1.16 (d, J=6.1 Hz, 6H), 2.4 (brs, 1H),
2.75 (s, 1H), 2.77 (s, 1H), 3.37 (s, 2H),
4.69 (dd, J=6.1 Hz, 1.2 Hz, 1H),
4.97 (sept, J=6.1 Hz, 1H),
6.1 (dd, J=16.5 Hz, 6.1 Hz, 1H),
6.55 (dd, J=16.5 Hz, 1.2 Hz, 1H),
7.1–7.3 (m, 5H)

EXAMPLE 3

Synthesis of Aluminum Triisopropoxide

In an atmosphere of argon, 10 ml of dichloromethane, 4.34 ml (56.52 mmol) of isopropyl alcohol and 2.38 ml (9.42 mmol) of triisobutylaluminum were placed in a schlenk tube cooled at 0° C., and stirred at 0° C. over 1 hour to obtain the dichloromethane solution containing aluminum triisopropoxide.

Synthesis of Isopropyl-5-hydroxy-3-oxo-5-phenylheptanoate

To the dichloromethane solution, 1.92 ml (18.84 mmol) of benzaldehyde and 1.5 ml (18.84 mmol) of diketene were added, and were vigorously stirred at 0° C. over 24 hours to obtain a reaction mixture. The reaction mixture was added to a mixed solution of 50 ml of 1N HCl and 50 ml of diethyl ether, and was vigorously stirred at 0° C. over 1 hour to give a solution. The solution was extracted with three portions of 50 ml of diethyl ether. The diethyl ether portions were combined, and washed three times with a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of hexane and ethyl acetate (hexane:ethyl acetate= 5:1) to give 1.2 g of isopropyl 5-hydroxy-3-oxo-5-phenylheptanoate (yield: 55% based on the amount of benzaldehyde).

EXAMPLE 4

Synthesis of Titanium Monochlorotriisopropoxide (TiCl(O—isoC$_3$H$_7$)$_3$)

In an atmosphere of argon, 34.5 g (0.12 mol) of titanium tetraisopropoxide were placed in a round-bottom flask and was cooled to 0° C. 4.4 ml (0.04 mol) of titanium tetrachloride was dropwise added into the flask with vigorously stirring over 5 minutes and then stirred at room temperature for 1 hour. The obtained reaction mixture was distilled under reduced pressure to collect distillates of 96°–97° C./3 mmHg. Thus, 40 g (0.15 mol) of titanium monochlorotriisopropoxide was obtained. The synthesis was conducted according to a method described in Chemische Berichte (Vol. 118, pp. 1421–1440, 1985).

Synthesis of Isopropyl E-5-hydroxy-3-oxo-7-phenyl-6-heptenoate

In an atmosphere of argon, 10 ml of dichloromethane and 1.92 g (7.5 mmol) of titanium monochlorotriisopropoxide were placed in a schlenk tube, and cooled to 0° C. with stirring. To the dichloromethane solution, 0.99 g (7.5 mmol) of E-cinnamaldehyde and 1.16 ml (15 mmol) of diketene were added, and vigorously stirred at 0° C. over 21 hours to obtain a reaction mixture. To the reaction mixture, 0.6 ml of isopropyl alcohol was added, and vigorously stirred at 0° C. over 1 hour. The reaction mixture was added to a mixed solution of 50 ml of 1N HCl and 50 ml of diethyl ether, and vigorously stirred at room temperature over 15 hours to give a solution. The solution was extracted with three portions of 10 ml of dichloromethane. The dichloromethane portions were combined, and dried by adding anhydrous magnesium sulfate. The solvent of the solution was removed by distillation in vacuo to obtain a concentrated solution. The concentrated solution was placed on a silica gel column and eluted with a mixture of hexane and ethyl acetate (hexane:ethyl acetate=7:3) to give 0.64 g of isopropyl E- 5-hydroxy-3-oxo-7-phenyl-6-heptenoate (yield: 31% based on the amount of E-cinnamaldehyde).

EXAMPLE 5

Synthesis of Titanium Dichlorodiisopropoxide (TiCl$_2$(O—isoC$_3$H$_7$)$_2$)

In an atmosphere of argon, 5 ml of hexane and 3.0 ml (10 mmol) of titanium tetraisopropoxide were placed in a round-bottom flask. 1.1 ml (10 mmol) of titanium tetrachloride was added into the flask with vigorously stirring and then the mixture was vigorously stirred at room temperature for 10 minutes. Thereafter, the mixture was allowed to stand at 0° C. for 10 minutes to precipitate a white crystal. After the solvent in the mixture was removed with a syringe, 5 ml of hexane was added to the mixture and stirred vigorously at room temperature for 10 minutes. Subsequently, the mixture was allowed to stand at 0° C. for 10 minutes to precipitate a white crystal, and the solvent in the mixture was removed with a syringe. These operations for the precipitation and remove were repeated once more. The obtained crystal was dried in vacuo to obtain 3.66 g (15 mmol) of titanium dichlorodiisopropoxide. The synthesis was conducted according to a method described in Japanese Patent Provisional Publication No. 2(1990)-40344. The obtained titanium dichlorodiisopropoxide was dissolved in 7.2 ml of dichloromethane to prepare a solution.

Synthesis of Isopropyl
E-5-hydroxy-3-oxo-7-phenyl-6-heptenoate

In an atmosphere of argon, 10 ml of dichloromethane and 2.5 ml (5.0 mmol) of the above titanium dichlorodiisopropoxide-dichloromethane solution were placed in a schlenk tube, and cooled to −25° C. with stirring. To the dichloromethane solution, 0.656 g (5.0 mmol) of E-cinnamaldehyde and 0.77 ml (10 mmol) of diketene were added, and were vigorously stirred at −25° C. over 69 hours to obtain a reaction mixture. To the reaction mixture, 1.5 ml of isopropyl alcohol was added, and was vigorously stirred at −25° C. over 1 hour. The reaction mixture was added to a mixed solution of 25 ml of 1N HCl and 25 ml of dichloromethane, and vigorously stirred at room temperature over 2 hours to give a solution. The solution was extracted with three portions of 5 ml of dichloromethane. The dichloromethane portions were combined, and dried by adding anhydrous magnesium sulfate. The solvent of the solution was removed by distillation in vacuo to obtain a concentrated solution. The concentrated solution was placed on a silica gel column and eluted with a mixture of hexane and ethyl acetate (hexane:ethyl acetate=7:3) to give 0.188 g of isopropyl E-5-hydroxy-3-oxo-7-phenyl-6-heptenoate (yield: 14% based on the amount of E-cinnamaldehyde).

EXAMPLE 6

Synthesis of Titanium Trichloromonoisopropoxide
($TiCl_3(O—isoC_3H_7)$)

In an atmosphere of argon, 5 ml of hexane and 1.5 ml (5.0 mmol) of titanium tetraisopropoxide were placed in a round-bottom flask. 1.65 ml (15 mmol) of titanium tetrachloride was added into the flask and then the mixture was stirred at room temperature over 10 minutes. Thereafter, the mixture was allowed to stand at 0° C. for 10 minutes to precipitate a white crystal. After the solvent in the mixture was removed with a syringe, 5 ml of hexane was added to the mixture and stirred vigorously at room temperature for 10 minutes. Subsequently, the mixture was allowed to stand at 0° C. for 10 minutes to precipitate a white crystal, and the solvent in the mixture was removed with a syringe. These operations for the precipitation and remove were repeated once more. The obtained crystal was dried in vacuo to obtain 3.89 g (18 mmol) of titanium trichloromonoisopropoxide. The data of $^1$H-NMR of the titanium trichloromonoisopropoxide was coincident with those described in Organometallics (Vol. 10, pp. 2015–2025, 1991). The obtained titanium trichloromonoisopropoxide was dissolved in 18.2 ml of dichloromethane to prepare a solution.

Synthesis of Isopropyl
E-5-hydroxy-3-oxo-7-phenyl-6-heptenoate

In an atmosphere of argon, 10 ml of dichloromethane and 5.0 ml (5.0 mmol) of the above titanium trichloromonoisopropoxide-dichloromethane solution were introduced in a schlenk tube, and cooled to −30° C. with stirring. To the dichloromethane solution, 0.677 g (5.1 mmol) of E-cinnamaldehyde and 0.77 ml (10 mmol) of diketene were added, and were vigorously stirred at −30° C. over 1 hours to obtain a reaction mixture. To the reaction mixture, 1.5 ml of isopropyl alcohol was added, and vigorously stirred at −30° C. over 40 minutes. The reaction mixture was added to a mixed solution of 25 ml of 1N HCl and 25 ml of dichloromethane, and vigorously stirred at room temperature over 2 hours to give a solution. The solution was extracted with three portions of 5 ml of dichloromethane. The dichloromethane portions were combined, and dried by adding anhydrous magnesium sulfate. The solvent of the solution was removed by distillation in vacuo to obtain a concentrated solution. The concentrated solution was placed on a silica gel column and eluted with a mixture of hexane and ethyl acetate (hexane:ethyl acetate=7:3) to give 0.310 g of isopropyl E-5-hydroxy-3-oxo-7-phenyl-6-heptenoate (yield: 22% based on the amount of E-cinnamaldehyde).

EXAMPLE 7

Synthesis of Aluminum Chlorodiisopropoxide

In an atmosphere of argon, 0.77 ml (10 mmol) of isopropyl alcohol was added to a solution obtained by dissolving 0.6 g (5.0 mmol) of diethylaluminum chloride in 5 ml of dichloromethane in a schlenk tube at 0° C., and stirred at the temperature. Then, the mixture was warmed to room temperature, was kept with stirring at the temperature for 1 hour and was cooled to 0° C. Thus, the dichloromethane solution containing aluminum chlorodiisopropoxide.

Synthesis of Isopropyl
5-hydroxy-3-oxo-5-phenylheptanoate

To the dichloromethane solution, 1.0 ml (9.8 mmol) of benzaldehyde and 1.52 ml (19.6 mmol) of diketene were added, and stirred at 0° C. over 24 hours to obtain a reaction mixture. The reaction mixture was added to a mixed solution of 50 ml of 1N HCl and 50 ml of diethyl ether at 0° C., and was vigorously stirred at 0° C. to give a solution. The solution was extracted with three portions of 100 ml of diethyl ether. The diethyl ether portions were combined, washed with 100 ml of a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of hexane and ethyl acetate (hexane:ethyl acetate=3:1) to give 1.1 g of isopropyl 5-hydroxy-3-oxo-5-phenylheptanoate (yield: 45% based on the amount of benzaldehyde).

COMPARISON EXAMPLE 1

In an atmosphere of argon, 9 ml of dichloromethane and 0.55 ml (5.0 mmol) of titanium tetrachloride were introduced in a schlenk tube, and cooled to 0° C. with stirring. To the dichloromethane solution, 0.68 g (5.2 mmol) of E-cinnamaldehyde and 0.77 ml (10 mmol) of diketene were added, and were vigorously stirred at 0° C. over 30 minutes to obtain a reaction mixture. To the reaction mixture, 2 ml of isopropyl alcohol was added, and vigorously stirred at 0° C. over 30 minutes. The reaction mixture was then added to a mixed solution of 25 ml of 1N HCl and 25 ml of dichloromethane, and vigorously stirred at room temperature over 30 minutes to give a solution. The solution was extracted with three portions of 5 ml of dichloromethane. The dichloromethane portions were combined, and dried by adding anhydrous magnesium sulfate. The solvent of the solution was removed by distillation in vacuo to obtain a concentrated solution. The concentrated solution was placed on a silica gel column and eluted with a mixture of hexane and ethyl acetate (hexane:ethyl acetate=7:3), a fraction corresponding to isopropyl E-5-hydroxy-3-oxo-7-phenyl-6-heptenoate was obtained in the same manner as Example 6. However, the fraction did not show the same peaks of NMR as those corresponding the isopropyl E-5-hydroxy-3-oxo-7-phenyl-6-heptenoate obtained in Example 6.

In the second place, the examples 8–31 showing the process for the preparation of optically active 5-hydroxy-3-ketoester derivative of the formula (VIII) are described below.

The optical purity (%ee) of each example was measured by means of HPLC under the following conditions.

1) The conditions for measurement of the optical purity of optically active 5-hydroxy-3-ketoester derivative obtained in Examples Column: CHIRALPAC AD Eluent: Mixture of hexane, ethanol and trifluoroacetic acid (hexane:ethanol trifluoroacetic acid=95:5:0.01)

Flow rate: 1.0 ml/minute

Detected by: UV (wavelength: 254 nm)

Temperature: Room temperature (25 °C.)

Concentration: 10 mg/1 ml (1 ml:eluent)

2) The yield (%) in the Examples was determined according to the formula:

$$\text{Yield} = \frac{\text{5-hydroxy-3-ketoester derivative (mole)}}{\text{Aldehyde compound (mole)}} \times 100$$

3) The yield (%) in the Reference Examples was determined according to the formula:

$$\text{Yield} = \frac{\text{Schiff Base derivative (mole)}}{\beta\text{-aminoalcohol derivative (mole)}} \times 100$$

Although the optically active 5-hydroxy-3-ketoester derivative occasionally exists in the form of a mixture of keto form and enol form, the keto form and the enol form show the same optical purity each other.

EXAMPLE 8

In an atmosphere of argon, 1.43 g (5.4 mmol) of (S)-2-N-(3'-tert-butylsalicylidene)amino]-3-methyl-1-butanol, 5 ml of dichloromethane and 1.45 ml (4.9 mmol) of titanium tetraisopropoxide were placed in a schlenk tube, were stirred at room temperature over 1 hour and were cooled to −20° C. to prepare a dichloromethane solution. To the dichloromethane solution, 0.5 ml (4.9 mmol) of benzaldehyde and 0.75 ml (9.8 mmol) of diketene were added in this order, and were vigorously stirred at −20° C. over 48 hours to give a reaction mixture. After the reaction mixture was warmed to room temperature, 0.75 ml (4.9 mmol) of isopropyl alcohol was added to the reaction mixture and was vigorously stirred at room temperature over 1 hour to give a reaction mixture. The reaction mixture was added to a mixed solution of 50 ml of 1N HCl and 50 ml of diethyl ether, and vigorously stirred at room temperature over 24 hours to give a solution. The solution was extracted with three portions of 50 ml of diethyl ether. The diethyl ether portions were combined, washed twice with 50 ml of a saturated sodium hydrogencarbonate aqueous solution, and further washed twice with 50 ml of a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of benzene and diethyl ether (benzene:diethyl ether=3:1) to give 1.04 g of optically active isopropyl 5-hydroxy-3-oxo-5-phenylpentanoate (yield: 85%; optical purity: 84% ee).

IR-spectra $\gamma_{max}$ (neat):

3508, 2984, 2936, 1746, 1646, 1314, 1106 (cm$^{-1}$)

$^1$H-NMR(CDCl$_3$, 250 MHz) δ:

1.26 (d, J=6.7 Hz, 6H) , 2.4 (brs, 1H), 2.94 (d, J=3.7 Hz, 1H), 2.97 (d, J=9.2 Hz, 1H), 3.46 (s, 2H) , 5.0–5.1 (m, 1H) , 5.2 (dd, J=3.7 Hz, 9.2 Hz, 1H), 7.3–7.4 (m, 5H)

$[\alpha]_D^{25.0}$:−40.8° (c=1.0; CHCl$_3$)

Retention time of HPLC ($t_R$):

12 minute (minor constituent)

19 minute (major constituent)

EXAMPLE 9

The procedure of Example 8 was repeated except changing the amount of (S)-2-[N-(3'-tert-butylsalicylidene)amino]-3-methyl-1-butanol from 1.43 g (5.4 mmol) to 0.65 g (2.5 mmol), and changing the amount of titanium tetraisopropoxide from 1.45 ml (4.9 mmol) to 0.725 ml (2.5 mmol), to obtain 0.76 g of optically active isopropyl 5-hydroxy-3-oxo-5-phenylpentanoate (yield: 62%; optical purity: 84% ee).

EXAMPLE 10

The procedure of Example 8 was repeated except using 1.11 g (5.4 mmol) of (S)-2-(N-(salicylidene)amino)-3-methyl- 1-butanol instead of 1.43 g (5.4 mmol) of (S)-2-[N-(3'-tert-butylsalicylidene)amino]-3-methyl-1-butanol to obtain 0.28 g of optically active isopropyl-5-hydroxy-3-oxo-5-phenylpentanoate (yield: 23%; optical purity: 16% ee).

EXAMPLE 11

The procedure of Example 8 was repeated except using 1.50 g (5.4 mmol) of (S)-2-[N-(3'-tert-butylsalicylidene)amino] -3,3-dimethyl-1-butanol instead of 1.43 g (5.4 mmol) of (S)-2-[N-(3'-tert-butylsalicylidene) amino]-3-methyl- 1-butanol to obtain 1.04 g of optically active isopropyl 5-hydroxy-3-oxo-5-phenylpentanoate (yield: 85%; optical purity: 80% ee).

EXAMPLE 12

The procedure of Example 8 was repeated except using 1.72 g (5.4 mmol) of (S)-2-[N-(3',5'-di-tert-butylsalicylidene)amino] -3-methyl-1-butanol instead of 1.43 g (5.4 mmol) of (S)-2-[N-(3'-tert-butylsalicylidene)amino]-3-methyl-1-butanol to obtain 0.92 g of optically active isopropyl 5-hydroxy- 3-oxo-5-phenylpentanoate (yield: 75%; optical purity: 82% ee).

EXAMPLE 13

The procedure of Example 8 was repeated except using 1.27 g (5.4 mmol) of (S)-2-[N-(3'-tert-butylsalicylidene)amino] -1-propanol instead of 1.43 g (5.4 mmol) of (S)-2-[N-(3'-tert-butylsalicylidene)amino]-3-methyl-1-butanol to obtain 0.58 g of optically active isopropyl 5-hydroxy-3-oxo- 5-phenylpentanoate (yield: 47%; optical purity: 38% ee).

EXAMPLE 14

The procedure of Example 8 was repeated except using 1.34 g (5.4 mmol) of (R)-2-[N-(3'-tert-butylsalicylidene)amino] -1-butanol instead of 1.43 g (5.4 mmol) of (S)-2-[N-(3'-tert-butylsalicylidene)amino]-3-methyl-1-butanol to obtain 1.05 g of optically active isopropyl 5-hydroxy-3-oxo- 5-phenylpentanoate (yield: 86%; optical purity: 72% ee).

EXAMPLE 15

The procedure of Example 8 was repeated except using 1.50 g (5.4 mmol) of (S)-2-[N-(3'-tert-butylsalicylidene)amino] -4-methyl-1-pentanol instead of 1.43 g (5.4 mmol) of (S)-2-[N-(3'-tert-butylsalicylidene)amino]-3-methyl-1-butanol to obtain 0.88 g of optically active isopropyl 5-hydroxy-3-oxo-5-phenylpentanoate (yield: 72%; optical purity: 74% ee).

EXAMPLE 16

The procedure of Example 8 was repeated except using 1.60 g (5.4 mmol) of (R)-2-[N-(3'-tert-butylsalicylidene)amino] -2-phenyl-1-ethanol instead of 1.43 g (5.4 mmol) of (S)-2-[N-(3'-tert-butylsalicylidene)amino]-3-methyl-1-butanol to obtain 0.69 g of optically active isopropyl 5-hydroxy- 3-oxo-5-phenylpentanoate (yield: 56%; optical purity: 10% ee).

EXAMPLE 17

The procedure of Example 8 was repeated except using 1.50 g (5.4 mmol) of (R)-1-[N-(3'-tert-butylsalicylidene)amino] -3,3-dimethyl-2-butanol instead of 1.43 g (5.4 mmol) of (S)-2-[N-(3'-tert-butylsalicylidene)amino]-3-methyl- 1-butanol to obtain 0.99 g of optically active isopropyl 5-hydroxy-3-oxo-5-phenylpentanoate (yield: 81%; optical purity: 67% ee).

EXAMPLE 18

The procedure of Example 8 was repeated except using 0.59 g (4.9 mmol) of p-methylbenzaldehyde instead of 0.5 ml (4.9 mmol) of benzaldehyde to obtain 1.16 g of optically active isopropyl 5-hydroxy-5-(4-methylphenyl)-3-oxopentanoate (yield: 90%; optical purity: 81% ee).

IR-spectra $\gamma_{max}$ (neat):
3492, 2988, 2936, 1716, 1646, 1314, 1106 (cm$^{-1}$)
$^1$H-NMR(CDCl$_3$, 250 MHz) δ:
1.25 (d, J=6.1 Hz, 6H), 2.34 (s, 3H),
2.91 (d, J=3.7 Hz, 1H), 2.96 (d, J=8.5 Hz, 1H),
3.44 (s, 2H), 5.05 (sept, J=6.1 Hz, 1H),
5.15 (dd, J=3.7 Hz, 8.5 Hz, 1H),
7.1–7.3 (m, 4H)
$[\alpha]_D^{25.0}$: −37.5° (c=1.2; CHCl$_3$)
Retention time of HPLC ($t_R$):
12 minute (minor constituent)
17 minute (major constituent)

EXAMPLE 19

The procedure of Example 8 was repeated except using 0.67 g (4.9 mmol) of p-methoxybenzaldehyde instead of 0.5 ml (4.9 mmol) of benzaldehyde to obtain 1.22 g of optically active isopropyl 5-hydroxy-5-(4-methoxyphenyl)-3-oxopentanoate (yield: 89%; optical purity: 67% ee).

IR-spectra $\gamma_{max}$ (neat):
3500, 2988, 2940, 1740, 1616, 1514, 1378, 1106 (cm$^{-1}$)
$^1$H-NMR(CDCl$_3$, 250 MHz) δ:
1.25 (d, J=6.1 Hz, 6H), 2.4 (brs, 1H),
2.91 (d, J=3.7 Hz, 1H), 2.96 (d, J=9.2 Hz, 1H),
3.45 (s, 2H), 3.8 (s, 3H),
5.0 (sept, J=6.1 Hz, 1H) ,
5.14 (dd, J=3.7 Hz, 9.2 Hz, 1H),
6.8–6.9 (m, 2H), 7.1–7.3 (m, 4H)
$[\alpha]_D^{25.0}$:−27.6° (c=1.3; CHCl$_3$)
Retention time of HPLC ($t_R$):
22 minute (minor constituent)
33 minute (major constituent)

EXAMPLE 20

The procedure of Example 8 was repeated except using 0.66 g (4.9 mmol) of 3-phenylpropanal instead of 0.5 ml (4.9 mmol) of benzaldehyde to obtain 0.94 g of optically active isopropyl 5-hydroxy-7-phenylheptanoate (yield: 69%; optical purity: 73% ee).

IR-spectra $\gamma_{max}$ (neat):
3448, 2988, 2936, 1740, 1712, 1646, 1378, 1316, 1106 (cm$^{-1}$)
$^1$H-NMR(CDCl$_3$, 250 MHz) δ:
1.25 (d, J=6.1 Hz, 6H), 1.7–1.9 (m, 2H),
2.2–2.4 (brs, 1H) , 3.42 (s, 2H) ,
4.0–4.1 (m, 1H), 5.0–5.1 (m, 1H),
7.2–7.3 (m, 5H)
$[\alpha]_D^{25.0}$:−5.1° (C=1.1; CHCl$_3$)
Retention time of HPLC ($t_R$):
12 minute (minor constituent)
19 minute (major constituent)

EXAMPLE 21

The procedure of Example 8 was repeated except using 0.55 g (4.9 mmol) of 2-thiophenecarboxaldehyde instead of 0.5 ml (4.9 mmol) of benzaldehyde to obtain 1.10 g of optically active isopropyl 5-hydroxy-3-oxo-5-(thiophen-2-yl)pentanoate (yield: 88%; optical purity: 70% ee).

IR-spectra $\gamma_{max}$ (neat):
3498, 2988, 1736, 1316, 1106 (cm$^{-1}$)
$^1$H-NMR(CDCl$_3$, 250 MHz) δ:
1.26 (d, J=6.1 Hz, 6H), 2.7 (brs, 1H),
3.07 (d, J=4.3 Hz, 1H), 3.1 (d, J=8.5 Hz, 1H),
3.47 (s, 2H), 5.0 (sept, J=6.1 Hz, 1H),
5.4 (dd, J=4.3 Hz, 8.5 Hz, 1H),
6.9–7.0 (m, 2H), 7.2–7.3 (m, 1H)
$[\alpha]_D^{25.0}$: −21.8° (c=1.0; CHCl$_3$)
Retention time of HPLC ($t_R$):
14 minute (minor constituent)
25 minute (major constituent)

EXAMPLE 22

The procedure of Example 8 was repeated except using 0.47 g (4.9 mmol) of furancarboxaldehyde instead of 0.5 ml (4.9 mmol) of benzaldehyde to obtain 1.08 g of optically active isopropyl 5-(furan-2-yl)-5-hydroxy-3-oxopentanoate (yield: 92%; optical purity: 61% ee).

IR-spectra $\gamma_{max}$ (neat):
3472, 2988, 1734, 1318, 1106 (cm$^{-1}$)
$^1$H-NMR(CDCl$_3$, 250 MHz) δ:
1.26 (d, J=6.1 Hz, 6H), 2.5 (brs, 1H),
3.07 (d, J=3.7 Hz, 1H), 3.14 (d, J=8.6 Hz, 1H),
3.48 (s, 2H), 5.0–5.1 (m, 1H),
5.2 (dd, J=3.7 Hz, 8.6 Hz, 1H),
6.2–6.3 (m, 2H) , 7.3–7.4 (m, 1H)
$[α]_D^{25.0}$: −18.4° (c=1.2; CHCl$_3$)
Retention time of HPLC (t$_R$):
15 minute (minor constituent)
22 minute (major constituent)

EXAMPLE 23

The procedure of Example 8 was repeated except using 0.34 g (4.9 mmol) of E-crotonaldehyde instead of 0.5 ml (4.9 mmol) of benzaldehyde to obtain 0.79 g of optically active isopropyl E-5-hydroxy-3-oxo-6-octenoate (yield: 75%; optical purity: 56% ee).

IR-spectra $\gamma_{max}$ (neat):
3456, 2988, 1740, 1314, 1106 (cm$^{-1}$)
$^1$H-NMR (CDCl$_3$, 250 MHz ) δ:
1.27 (d, J=6.1 Hz, 6H), 1.6 (brs, 1H),
1.70 (d, J=6.1 Hz, 3H), 2.75 (d, J=6.1 Hz, 2H),
3.45 (s, 2H), 4.55 (dd, J=12.2 Hz, 6.1 Hz, 1H),
5.0–5.1 (m, 1H), 5.4–5.6 (m, 1H),
5.7–5.8 (m, 1H)
$[α]_D^{25.0}$: −10.2° (C=1.0; CHCl$_3$)
Retention time of HPLC (t$_R$):
8 minute (minor constituent)
11 minute (major constituent)

EXAMPLE 24

The procedure of Example 8 was repeated except using 0.34 g (4.9 mmol) of methacrylaldehyde (CH=C(CH$_3$)CHO) instead of 0.5 ml (4.9 mmol) of benzaldehyde to obtain 0.86 g of optically active isopropyl E-5-hydroxy-6-methyl-3-oxo- 6-heptenoate (yield: 82%; optical purity: 68% ee).

IR-spectra $\gamma_{max}$ (neat):
3528, 2988, 1738, 1654, 1320, 1106 (cm$^{-1}$)
$^1$H-NMR(CDCl$_3$, 250 MHz) δ:
1.27 (d, J=6.1 Hz, 6H), 1.75 (s, 3H),
2.5 (brs, 1H), 2.78 (d, J=6.1 Hz, 2H) ,
3.47 (s, 1H), 4.54 (t, J=6.1 Hz, 1H),
4.88 (s, 1H), 5.0–5.1 (m, 2H)
$[α]_D^{25.0}$: −27.1° (C=1.1; CHCl$_3$)
Retention time of HPLC (t$_R$):
8 minute (minor constituent)
11 minute (major constituent)

EXAMPLE 25

The procedure of Example 8 was repeated except using 0.55 g (4.9 mmol) of cyclohexanecarboxaldehyde instead of 0.5 ml (4.9 mmol) of benzaldehyde to obtain 1.15 g of optically active isopropyl 5-cyclohexyl-5-hydroxy-3-oxo-pentanoate (yield: 92%; optical purity: 58% ee).

IR-spectra $\gamma_{max}$ (neat):
3480, 2988, 1740, 1714, 1646, 1316, 1106 (cm$^{-1}$)
$^1$H-NMR(CDCl$_3$, 250 MHz) δ:
1.0–1.5 (m, 5H), 1.26 (d, J=6.1 Hz, 6H),
1.6–1.9 (m, 6H), 2.2 (brs, 1H),
2.67 (d, J=6.5 Hz, 1H) ,
2.71 (d, J=3.66 Hz, 1H),
3.45 (s, 2H), 3.8–3.9 (m, 1H),
5.05 (sept, J=6.1 Hz, 1H)
$[α]_D^{25.0}$:−21.9° (C=1.1; CHCl$_3$)
Retention time of HPLC (t$_R$):
10 minute (minor constituent)
15 minute (major constituent)

EXAMPLE 26

The procedure of Example 8 was repeated except using 0.41 g (4.9 mmol) of tiglic aldehyde instead of 0.5 ml (4.9 mmol) of benzaldehyde to obtain 0.82 g of optically active isopropyl 5-hydroxy-6-methyl-3-oxo-6-octenoate (yield: 73%; optical purity: 63% ee).

IR-spectra $\gamma_{max}$ (neat):
3456, 2988, 1738, 1646, 1482, 1314, 1106 (cm$^{-1}$)
$^1$H-NMR(CDCl$_3$, 250 MHz) δ:
1.26 (d, J=6.1 Hz, 6H), 1.61 (d, J=6.72 Hz, 3H),
1.62 (s, 3H), 2.2 (brs, 1H),
2.72 (d, J=3.16 Hz, 1H) ,
2.77 (d, J=9.16 Hz, 1H),
3.46 (s, 2H), 4.50 (dd, J=9.16 Hz, 3.16 Hz, 1H),
5.0–5.6 (m, 1H)
$[α]_D^{25.0}$: −16.7° (c=1.1; CHCl$_3$)
Retention time of HPLC (t$_R$):
8 minute (minor constituent)
11 minute (major constituent)

EXAMPLE 27

The procedure of Example 8 was repeated except using 0.35 g (4.9 mmol) of butanal instead of 0.5 ml (4.9 mmol) of benzaldehyde to obtain 0.89 g of optically active isopropyl 5-hydroxy-3-oxo-6-octanoate (yield: 84%; optical purity: 67% ee).

IR-spectra $\gamma_{max}$ (neat):
3524, 2984, 2936, 1742, 1644, 1316, 1106 (cm$^{-1}$)
$^1$H-NMR(CDCl$_3$, 250 MHz) δ:
0.93 (t, J=7.0 Hz, 3H),
1.26 (d, J=6.1 Hz, 6H), 1.3–1.6 (m, 4H),
2.1 (brs, 1H), 2.66 (d, J=8.54 Hz, 1H),
2.71 (d, J=3.06 Hz, 1H), 3.44 (s, 2H),
4..0–4.1 (m, 1H), 5.0–5.1 (m, 1H)
$[α]_D^{25.0}$: −18.9° (c=1.1; CHCl$_3$)
Retention time of HPLC (t$_R$):
8 minute (minor constituent)
11 minute (major constituent)

EXAMPLE 28

The procedure of Example 8 was repeated except using 0.42 g (4.9 mmol) of trimethylacetoaldehyde instead of 0.5 ml (4.9 mmol) of benzaldehyde to obtain 0.90 g of optically active isopropyl 5-hydroxy-6,6-dimethyl-3-oxoheptanoate (yield: 80%; optical purity: 53% ee).

IR-spectra $\gamma_{max}$ (neat):

3548, 2984, 2876, 1740, 1646, 1316, 1106 (cm$^{-1}$)
$^1$H-NMR(CDCl$_3$, 250 MHz) δ:
0.91 (s, 9H), 1.26 (d, J=6.1 Hz, 6H),
2.5 (brs, 1H), 2.62 (d, J=10.38 Hz, 1H),
2.70 (d, J=2.45 Hz, 1H), 3.47 (s, 2H),
3.75 (dd, J=10.38 Hz, J=2.45 Hz, 1H),
5.0–5.1 (m, 1H)
$[α]_D^{25.0}$: −15.2° (C=1.0; CHCl$_3$)
Retention time of HPLC (t$_R$):
8 minute (minor constituent)
11 minute (major constituent)

EXAMPLE 29

The procedure of Example 8 was repeated except using 0.64 g (4.9 mmol) of phenylpropargylaldehyde instead of 0.5 ml (4.9 mmol) of benzaldehyde to obtain 0.76 g of optically active isopropyl 5-hydroxy-3-oxo-7-phenyl-6-heptynoate (yield: 57%; optical purity: 72% ee).

IR-spectra $γ_{max}$ (neat):
3468, 2983, 2937, 1736, 1649, 1105 (cm$^{-1}$)
$^1$H-NMR(CDCl$_3$, 400 MHz) δ:
1.24 (d, J=6.4 Hz, 6H),
3.01 (dd, J=4.4 Hz, J=17.1 Hz, 1H),
3.11 (dd, J=7.8 Hz, J=17.1 Hz, 1H),
3.50 (s, 2H), 3.0–4.3 (brs, 1H),
4.9–5.2 (m, 2H), 7.1–7.6 (m, 5H)
$[α]_D^{22.0}$: −17.1° (C=1.1; CHCl$_3$)
Retention time of HPLC (t$_R$):
14 minute (minor constituent)
19 minute (major constituent)

EXAMPLE 30

In an atmosphere of argon, 0.725 g (2.7 mmol) of (S)-2-[N-(3'-tert-butylsalicylidene)amino]-3-methyl-1-butanol, 2.5 ml of dichloromethane and 0.74 ml (2.45 mmol) of titanium tetraisopropoxide were placed in a schlenk tube, were stirred at room temperature over 1 hour and were cooled to −20° C. to prepare a dichloromethane solution. To the dichloromethane solution, 0.31 ml (2.45 mmol) of cinnamaldehyde and 1.0 ml (12.5 mmol) of diketene were added in this order, and were vigorously stirred at −20° C. over 48 hours. Subsequently, 0.23 ml (4.9 mmol) of isopropyl alcohol was added to the mixture and vigorously stirred at room temperature over 1 hour to give a reaction mixture. The reaction mixture was added to a mixed solution of 50 ml of 1N HCl and 50 ml of diethyl ether, and vigorously stirred at room temperature over 24 hours to give a solution. The solution was extracted with three portions of 50 ml of diethyl ether. The diethyl ether portions were combined, washed twice with 50 ml of a saturated sodium hydrogencarbonate aqueous solution, and further washed twice with 50 ml of a saturated sodium chloride aqueous solution to obtain a washed solution. To the solution, anhydrous magnesium sulfate was added to dry. The solvent of the solution was removed by distillation in vacuo to obtain a concentrated solution. The concentrated solution was placed on a silica gel column and eluted with a mixture of benzene and diethyl ether (benzene:diethyl ether=3:1) to give 0.58 g of optically active isopropyl 5-hydroxy-3-oxo- 7-phenyl-6-heptenoate (yield: 86%; optical purity: 78% ee).

IR-spectra $γ_{max}$ (neat):
3472, 2984, 2936, 1716, 1646, 1314, 1106 (cm$^{-1}$)
$^1$H-NMR(CDCl$_3$, 250 MHz) δ:
1.16 (d, J=6.1 Hz, 6H), 2.4 (brs, 1H),
2.75 (s, 1H), 2.77 (s, 1H),
3.37 (s, 2H), 4.69 (dd, J=6.1 Hz, 1.2 Hz, 1H),
4.97 (sept, J=6.1 Hz, 1H),
6.1 (dd, J=16.5 Hz, 6.1 Hz, 1H),
6.55 (dd, J=16.5 Hz, 1.2 Hz, 1H),
7.1–7.3 (m, 5H)
$[α]_D^{25.0}$: 11.0° (c=1.1; CHCl$_3$)
Retention time of HPLC (t$_R$):
16 minute (minor constituent)
24 minute (major constituent)

EXAMPLE 31

The procedure of Example 30 was repeated except changing the amount of (S)-2-[N-(3'-tert-butylsalicylidene)amino]-3-methyl-1-butanol from 0.725 g (2.7 mmol) to 0.33 g (1.25 mmol) and the amount of titanium tetraisopropoxide from 0.74 ml (2.5 mmol) to 0.37 ml (1.25 mmol), to obtain 0.39 g of optically active isopropyl 5-hydroxy-3-oxo- 7-phenyl-6-heptenoate (yield: 58%; optical purity: 74% ee).

EXAMPLE 32

The procedure of Example 8 was repeated except using 0.47 g (4.9 mmol) of 2,4-hexadienal instead of 0.5 ml (4.9 mmol) of benzaldehyde to obtain 0.71 g of optically active isopropyl 5-hydroxy-3-oxo-6,8-decadienoate (yield: 60%; optical purity: 76% ee).

IR-spectra $γ_{max}$ (neat):
3437, 2981, 2935, 2880, 1735, 1712, 1645, 1313, 1106 (cm$^{-1}$)
HMRS:
M+=240.1359 (found)
$[α]_D^{22.0}$: +8.8° (c=1.0; CHCl$_3$)
Retention time of HPLC (t$_R$):
20 minute (minor constituent)
25 minute (major constituent)

REFERENCE EXAMPLE 1

Synthesis of (S)-2-IN-3',5'-(ditert-butylsalicylidene)amino]-3-methyl-1-butanol]

4.6 g of (S)-2-amino-3-methyl-1-butanol and 9.6 g of 3,5-di-tert-butylsalicylaldehyde were dissolved in 65 ml of methanol to prepare a methanol solution. The methanol solution was heated under reflux over 6 hours to obtain a reaction mixture. The solvent of the mixture was removed by distillation in vacuo to obtain a concentrated solution. The concentrated solution was placed on a silica gel column and eluted with a mixture of hexane and ethyl acetate (hexane:ethyl acetate=10:1) to give 9.76 g of (S)-2-[N-3',5'-(ditert-butylsalicylidene)amino]-3-methyl-1-butanol in the form of yellow solid (yield: 74%).

Melting point: 107°–108° C.
IR-spectra $γ_{max}$ (neat):
3478, 2964, 2872, 1632, 1494, 1280 (cm$^{-1}$)
$^1$H-NMR(CDCl$_3$, 250 MHz) δ:
0.94 (d, J=6.7 Hz, 3H),
0.96 (d, J=6.7 Hz, 3H),
1.31 (s, 9H), 1.45 (s, 9H), 1.6 (brs, 1H), 1.90 (q, J=6.7 Hz, 1H),
3.0 (m, 1H), 3.8 (m, 2H),
7.14 (s, 1H), 7.41 (s, 1H),
8.38 (s, 1H), 13.5 (s, 1H)
$[\alpha]_D^{24.0}$:−34.3° (c=1.3; CHCl$_3$)

REFERENCE EXAMPLE 2

Synthesis of
(R)-2-[N-(3'-tert-butylsalicylidene)amino]
-3,3-dimethyl-2-butanol 0.71 g of (R)-2-hydroxy-3,3-dimethyl-1-aminobutane and 0.99 g of 3-tert-butylsalicylaldehyde were disolved in 10 ml of methanol to prepare a methanol solution. The methanol solution was heated under reflux over 6 hours to obtain a reaction mixture. The solvent of the mixture was removed by distillation in vacuo to obtain a concentrated solution. The concentrated solution was placed on a silica gel column and eluted with a mixture of hexane and ethyl acetate (hexane:ethyl acetate=5:1) to give 0.83 g of (R)-2-[N-(3-tert-butylsalicylidene)amino]-3,3'-dimethyl-2-butanol in the form of yellow syrup (yield: 54%).

IR-spectra $\gamma_{max}$ (neat):
3456, 2956, 1634, 1436, 1268 (cm$^{-1}$)
$^1$H-NMR (CDCl$_3$, 250 MHz) δ:
1.01 (s, 9H), 1.43 (s, 9H),
1.9 (brs, 1H), 3.32 (t, J=11.6 Hz, 1H),
3.61 (d, J=11.6 Hz, 1H),
3.97 (t, J=11.6 Hz, 1H),
6.84 (t, J=7.3 Hz, 1H)
8.41 (s, 1H), 13.9 (brs, 1H)
$[\alpha]_D^{24.0}$: −104.9° (c=1.0; CHCl$_3$)

REFERENCE EXAMPLE 3

Synthesis of
(R)-2-[N-(3'-tert-butylsalicylidene)amino]
-1-butanol 0.98 g of (R)-2-amino-1-butanol and 1.78 g of 3-tertbutylsalicylaldehyde were disolved in 15 ml of methanol to prepare a methanol solution. The methanol solution was heated under reflux over 6 hours to obtain a reaction mixture. The solvent of the mixture was removed by distillation in vacuo to obtain a concentrated solution. The concentrated solution was placed on a silica gel column and eluted with a mixture of hexane and ethyl acetate (hexane:ethyl acetate=3:1) to give 2.04 g of (R)-2-[N-(3-tert-butylsalicylidene)amino] -1-butanol as yellow syrup (yield: 82%).

IR-spectra $\gamma_{max}$ (neat):
3372, 2964, 2876, 1632, 1436, 1268 (cm$^{-1}$)
$^1$H-NMR (CDCl$_3$, 250 MHz ) δ:
0.9 (t, J=7.1 Hz, 3H), 1.44 (s, 9H),
1.6–1.7 (m, 2H), 1.7 (brs, 1H),
3.1–3.3 (m, 1H), 6.8–7.5 (m, 3H),
8.4 (s, 1H), 13.8 (brs, 1H)
$[\alpha]_D^{24.0}$:+20.6° (C=1.1; CHCl$_3$)

REFERENCE EXAMPLE 4

Synthesis of
(S)-2-[N-(3'-tert-butylsalicylidene)amino]
-4-methyl-pentanol

The procedure of Reference Example 3 was repeated except using 1.29 g of (S)-2-amino-4-methyl-1-pentanol instead of 0.98 g of (R)-2-amino-1-butanol, to obtain 2.04 g of (S)-2-[N-(3'-tert-butylsalicylidene)amino]-4-methyl-pentanol as yellow syrup (yield: 78%).

IR-spectra $\gamma_{max}$ (neat):
3368, 2956, 1628, 1434, 1272 (cm$^{-1}$)
$^1$H-NMR(CDCl$_3$, 250 MHz) δ:
0.88 (t, J=6.1 Hz, 3H),
0.92 (t, J=6.1 Hz, 3H) ,
1.3–1.4 (m, 1H), 1.44 (s, 9H)
1.5–1.6 (m, 2H), 1.7 (brs, 1H),
3.4 (m, 1H), 3.7 (m, 2H),
6.8–7.5 (m, 3H), 8.4 (s, 1H),
13.8 (brs, 1H)
$[\alpha]_D^{25.0}$: −61.4° (c=1.1; CHCl$_3$)

We claim:

1. A process for the preparation of a 5-hydroxy-3-ketoester derivative of the formula (IV):

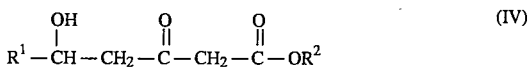

in which R$^1$ represents an alkyl group, an alkyl group having a substituent group, an alkenyl group, an alkenyl group having a substituent group, an alkynyl group, an alkynyl group having a substituent group, an aryl group, an aryl group having a substituent group, a heterocyclic group or a heterocyclic group having a substituent group, and R$^2$ represents an alkyl group, an alkyl group having a substituent group, an aryl group, or an aryl group having a substituent group, which comprises causing reaction of an aldehyde compound of the formula (I):

in which R$^1$ has the meaning defined above, and diketene of the formula:

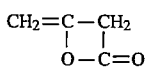

in the presence of a metal compound selected from the group consisting of titanium and aluminum compounds having at least one group of —OR$^3$ in which R$^3$ an alkyl group, an alkyl group having a substituent group, an aryl group or an aryl group having a substituent group;

—OR$^2$ of the formula (IV) being equal to —OR$^3$, or —OR$^2$ being introduced by incorporation of a compound having the —OR$^2$ group into a mixture of the reaction.

2. The process for the preparation of a 5-hydroxy- 3-ketoester derivative as defined in claim 1, wherein R$^1$ of the formula (I) and the formula (IV) represents an alkyl group of 1 to 12 carbon atoms, an alkyl group of 1 to 12 carbon atoms having a substituent group, an alkenyl group of 2 to 12 carbon atoms, or an alkenyl group of 2 to 12 carbon atoms having a substituent group.

3. The process for the preparation of a 5-hydroxy-3 -ketoester derivative as defined in claim 1, wherein R$^1$ of the formula (I) and the formula (IV) represents an alkyl group of 1 to 12 carbon atoms, an alkyl group of 1 to 12 carbon atoms having an aromatic group, an alkenyl group of 2 to 12 carbon atoms, or an alkenyl group of 2 to 12 carbon atoms having an aromatic group.

4. The process for the preparation of a 5-hydroxy- 3-ketoester derivative as defined in claim 1, wherein $R^1$ of the formula (I) and the formula (IV) represents an alkenyl group of 2 to 12 carbon atoms having a heterocyclic group.

5. The process for the preparation of a 5-hydroxy- 3-ketoester derivative as defined in claim 1, wherein $R^2$ of the formula (IV) represents an alkyl group of 1 to 12 carbon atoms, an aryl group of 6 to 15 carbon atoms, an alkyl group having an aryl group of 7 to 20 carbon atoms, an aryl group of 6 to 15 carbon atoms having at least one substituent group selected from the group consisting of halogen, cyano, nitro and alkyl of 1 to 6 carbon atoms, or an alkyl group having an aryl group of 7 to 20 carbon atoms which is substituted with at least one substituent group selected from the group consisting of halogen, cyano, nitro and alkyl of 1 to 6 carbon atoms.

6. The process for the preparation of a 5-hydroxy- 3-ketoester derivative as defined in claim 1, wherein $R^3$ of the metal compound represents an alkyl group of 1 to 12 carbon atoms, an aryl group of 6 to 15 carbon atoms, an alkyl group having an aryl group of 7 to 20 carbon atoms, an aryl group of 6 to 15 carbon atoms having at least one substituent group selected from the group consisting of halogen, cyano, nitro and alkyl of 1 to 6 carbon atoms, or an alkyl group having an aryl group of 7 to 20 carbon atoms which is substituted with at least one substituent group selected from the group consisting of halogen, cyano, nitro and alkyl of 1 to 6 carbon atoms.

7. The process for the preparation of a 5-hydroxy- 3-ketoester derivative as defined in claim 1, wherein the metal compound is a titanium compound having the formula (II):

$$Ti(OR^3)_n A^1_{4-n} \qquad (II)$$

in which $R^3$ has the meaning as defined in claim 1, $A^1$ represents a halogen atom or an alkyl group having 1 to 6 carbon atoms and n is an integer of 1 to 4; or an aluminum compound having the formula (III):

$$Al(OR^3)_m A^1_{3-m} \qquad (III)$$

in which $R^3$ and $A^1$ have the meanings defined above, and m is an integer of 1 to 3.

8. The process for the preparation of a 5-hydroxy- 3-ketoester derivative as defined in claim 1, wherein the metal compound is a titanium compound of $Ti(OR^3)_4$ or a aluminum compound of $Al(OR^3)_3$, in which $R^3$ has the meaning defined in claim 1.

9. The process for the preparation of a 5-hydroxy- 3-ketoester derivative as defined in claim 1, wherein $R^2$ of the formula (IV) is equal to $R^3$.

10. The process for the preparation of a 5-hydroxy- 3-ketoester derivative as defined in claim 1, wherein the reaction is performed at a temperature in the range of −40° to 40° C.

11. A process for the preparation of an optically active 5-hydroxy-3-ketoester derivative of the formula (VIII):

in which $R^{11}$ represents an alkyl group, an alkyl group having a substituent group, an alkenyl group, an alkenyl group having a substituent group, an alkynyl group, an alkynyl group having a substituent group, an aryl group, an aryl group having a substituent group, a heterocyclic group or a heterocyclic group having a substituent group, and $R^{12}$ represents an alkyl group, an alkyl group having a substituent group, an aryl group, or an aryl group having a substituent group, which comprises causing reaction of an aldehyde compound of the formula (V):

$$R^{11}CHO \qquad (V)$$

in which $R^{11}$ has the meaning defined above, and diketene of the formula:

in the presence of a metal compound selected from the group consisting of titanium and aluminum compounds having at least one group of $-OR^{13}$ in which $R^{13}$ an alkyl group, an alkyl group having a substituent group, an aryl group, or an aryl group having a substituent group and an optically active Schiff base, or a complex compound obtained by reacting the metal compound with the optically active Schiff base;

$-OR^{12}$ of the formula (VIII) being equal to $-OR^{13}$, or $-OR^{12}$ being introduced by incorporation of a compound having the $-OR^{12}$ group into a mixture of the reaction.

12. The process for the preparation of an optically active 5-hydroxy-3-ketoester derivative as defined in claim 11, wherein $R^{11}$ of the formula (V) and the formula (VIII) represents an alkyl group of 1 to 12 carbon atoms, an alkyl group of 1 to 12 carbon atoms having a substituent group, an alkenyl group of 2 to 12 carbon atoms, or an alkenyl group of 2 to 12 carbon atoms having a substituent group.

13. The process for the preparation of an optically active 5-hydroxy-3-ketoester derivative as defined in claim 12, wherein wherein $R^{11}$ of the formula (V) and the formula (VIII) represents an alkyl group of 1 to 12 carbon atoms, an alkyl group of 1 to 12 carbon atoms having an aromatic group, an alkenyl group of 2 to 12 carbon atoms, or an alkenyl group of 2 to 12 carbon atoms having an aromatic group.

14. The process for the preparation of an optically active 5-hydroxy-3-ketoester derivative as defined in claim 12, wherein wherein $R^{11}$ of the formula (V) and the formula (VIII) represents an alkenyl group of 2 to 12 carbon atoms having a heterocyclic group.

15. The process for the preparation of an optically active 5-hydroxy-3-ketoester derivative as defined in claim 11, wherein $R^{12}$ of the formula (VIII) represents an alkyl group of 1 to 12 carbon atoms, an aryl group of 6 to 15 carbon atoms, an alkyl group having an aryl group of 7 to 20 carbon atoms, an aryl group of 6 to 15 carbon atoms having at least one substituent group selected from the group consisting of halogen, cyano, nitro and alkyl of 1 to 6 carbon atoms, or an alkyl group having an aryl group of 7 to 20 carbon atoms which is substituted with at least one substituent group selected from the group consisting of halogen, cyano, nitro and alkyl of 1 to 6 carbon atoms.

16. The process for the preparation of an optically active 5-hydroxy-3-ketoester derivative as defined in claim 11, wherein $R^{13}$ of the metal compound represents an alkyl group of 1 to 12 carbon atoms, an aryl group of 6 to 15 carbon atoms, an alkyl group having an aryl group of 7 to 20 carbon atoms, an aryl group of 6 to 15 carbon atoms having at least one substituent group selected from the group consisting of halogen, cyano, nitro and alkyl of 1 to 6 carbon atoms, or an alkyl group having an aryl group of 7 to 20 carbon atoms which is substituted with at least one substituent group selected from the group consisting of halogen, cyano, nitro and alkyl of 1 to 6 carbon atoms.

17. The process for the preparation of an optically active 5-hydroxy-3-ketoester derivative as defined in claim 11, wherein the metal compound is a titanium compound having the formula (VI):

  (VI)

in which $R^{13}$ has the meaning defined in claim 11, $A^2$ represents a halogen atom or an alkyl group having 1 to 6 carbon atoms and p is an integer of 1 to 4; or an aluminum compound having the formula (VII):

  (VII)

in which $R^{13}$ and $A^2$ have the meanings defined above, and m is an integer of 1 to 3.

18. The process for the preparation of an optically active 5-hydroxy-3-ketoester derivative as defined in claim 17, wherein the metal compound is a titanium compound of $Ti(OR^{13})_3A^2$ or $Ti(OR^{13})_4$ in which $R^{13}$ and $A^2$ have the meanings defined in claim 17.

19. The process for the preparation of an optically active 5-hydroxy-3-ketoester derivative as defined in claim 11, wherein the metal compound is a titanium compound of $Ti(OR^{13})_4$ in which $R^{13}$ has the meaning as defined in claim 11.

20. The process for the preparation of a 5-hydroxy-3-ketoester derivative as defined in claim 11, wherein $R^{12}$ of the formula (VIII) is equal to $R^{13}$ of the metal compound.

21. The process for the preparation of an optically active 5-hydroxy-3-ketoester derivative as defined in claim 11, wherein the optically active Schiff base has the formula (IX):

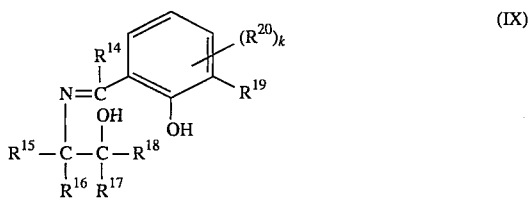  (IX)

in which each of $R^{14}$, $R^{15}$, $R^{16}$, $R^{17}$, $R^{18}$ and $R^{19}$ represents a hydrogen atom, an alkyl group, an aryl group or an aralkyl group, $R^{20}$ represents a hydrogen atom, an alkyl group, an aralkyl group, an alkyloxy group, an aryloxy group, a halogen atom, a nitro group, an alkyloxycarbonyl group, an aryloxycarbonyl group, a cyano group or an acyloxy group, and k represents an integer of 1 to 3, at least one of a carbon atom bonding to $R^{15}$ and $R^{16}$ and a carbon atom bonding to $R^{17}$ and $R^{18}$ being an asymmetric carbon atom.

22. The process for the preparation of an optically active 5-hydroxy-3-ketoester derivative as defined in claim 21, wherein each of $R^{14}$ and $R^{16}$ of the formula (IX) represents a hydrogen atom, $R^{15}$ of the formula (IX) represents a hydrogen atom, an alkyl group, or phenyl group and each of $R^{17}$, $R^{18}$, $R^{19}$ and $R^{20}$ of the formula (IX) represents a hydrogen atom or an alkyl group.

23. The process for the preparation of an optically active 5-hydroxy-3-ketoester derivative as defined in claim 11, wherein the reaction is performed in the presence of the complex compound of the metal compound and the optically active Schiff base.

24. The process for the preparation of an optically active 5-hydroxy-3-ketoester derivative as defined in claim 11, wherein the reaction is performed after the complex compound of the metal compound and the optically active Schiff base form together a complex compound.

25. The process for the preparation of an optically active 5-hydroxy-3-ketoester derivative as defined in claim 11, wherein the reaction is performed at a temperature in the range of −40° to 40° C.

* * * * *